(12) United States Patent
Grandfield et al.

(10) Patent No.: US 8,357,178 B2
(45) Date of Patent: Jan. 22, 2013

(54) VASCULAR AND BODILY DUCT TREATMENT DEVICES AND METHODS

(75) Inventors: Ryan M. Grandfield, Livermore, CA (US); Scott D. Wilson, Redwood City, CA (US); John H. Miller, Redwood City, CA (US); Emily Vu, San Jose, CA (US); Kirk L. Pedersen, San Francisco, CA (US); Craig L. Bonsignore, Pleasanton, CA (US); Elliot H. Sanders, Palo Alto, CA (US)

(73) Assignee: Concentric Medical, Inc., Mountain View, CA (US)

( * ) Notice: Subject to any disclaimer, the term of this patent is extended or adjusted under 35 U.S.C. 154(b) by 136 days.

(21) Appl. No.: 12/832,857

(22) Filed: Jul. 8, 2010

(65) Prior Publication Data

US 2011/0009950 A1 Jan. 13, 2011

Related U.S. Application Data

(63) Continuation-in-part of application No. 12/643,942, filed on Dec. 21, 2009, which is a continuation-in-part of application No. 12/573,676, filed on Oct. 5, 2009, which is a continuation-in-part of application No. 12/499,713, filed on Jul. 8, 2009.

(51) Int. Cl.
*A61B 17/22* (2006.01)
(52) U.S. Cl. ........................................ 606/200; 606/127
(58) Field of Classification Search .................. 606/127, 606/128, 159, 200; 623/1.11–1.54
See application file for complete search history.

(56) References Cited

U.S. PATENT DOCUMENTS

| 4,347,846 | A | 9/1982 | Dormia |
| 4,706,671 | A | 11/1987 | Weinrib |
| 4,776,337 | A | 10/1988 | Palmaz |
| 4,886,062 | A | 12/1989 | Wiktor |
| 5,011,488 | A | 4/1991 | Ginsburg |

(Continued)

FOREIGN PATENT DOCUMENTS

| AU | 2003254553 A1 | 2/2004 |
| CA | 2492978 A1 | 1/2004 |

(Continued)

OTHER PUBLICATIONS

International Search Report and Written Opinion for PCT International Application No. PCT/US2010/041434 issued by the ISA dated Sep. 8, 2010, Virginia, US.

(Continued)

*Primary Examiner* — Kathleen Sonnett
(74) *Attorney, Agent, or Firm* — Tim L. Kitchen; Peter B. Scull; Hamilton, DeSanctis & Cha, LLP

(57) ABSTRACT

A clot retrieval device including a self-expandable member having a proximal end portion and a main body portion. The self-expandable member is expandable from a first delivery position to a second placement position. In the first delivery position the expandable member has a first overall diameter In one implementation the cell structures that form the self-expandable member have dimensional and material characteristics that result in about a −1.0N to about a −1.7N overall reduction in radial force along the length of the expandable member per millimeter of expansion during about an initial 0.50 mm diametric range of expansion from the first overall diameter and that results in about a −0.10N to about a −0.35N overall reduction in radial force along the length of the expandable member per millimeter of expansion during subsequent diametric ranges of expansion.

11 Claims, 38 Drawing Sheets

U.S. PATENT DOCUMENTS

| | | | |
|---|---|---|---|
| 5,192,286 A | 3/1993 | Phan et al. | |
| 5,354,308 A | 10/1994 | Simon et al. | |
| 5,370,653 A | 12/1994 | Cragg | |
| 5,370,683 A | 12/1994 | Fontaine | |
| 5,456,667 A | 10/1995 | Ham et al. | |
| 5,496,365 A | 3/1996 | Sgro | |
| 5,643,312 A | 7/1997 | Fischell et al. | |
| 5,667,486 A | 9/1997 | Mikulich et al. | |
| 5,681,335 A | 10/1997 | Serra et al. | |
| 5,795,331 A | 8/1998 | Cragg et al. | |
| 5,800,519 A * | 9/1998 | Sandock | 623/1.22 |
| 5,800,520 A * | 9/1998 | Fogarty et al. | 623/1.37 |
| 5,800,525 A | 9/1998 | Bachinski et al. | |
| 5,810,872 A | 9/1998 | Kanesaka et al. | |
| 5,827,321 A | 10/1998 | Roubin et al. | |
| 5,836,966 A | 11/1998 | St. Germain | |
| 5,843,117 A | 12/1998 | Alt et al. | |
| 5,855,600 A | 1/1999 | Alt | |
| 5,876,449 A | 3/1999 | Starck et al. | |
| 5,879,370 A | 3/1999 | Fischell et al. | |
| 5,895,398 A | 4/1999 | Wensel et al. | |
| 5,895,406 A | 4/1999 | Gray et al. | |
| 5,911,754 A | 6/1999 | Kanesaka et al. | |
| 5,913,895 A | 6/1999 | Burpee et al. | |
| 5,968,088 A | 10/1999 | Hansen et al. | |
| 5,972,019 A | 10/1999 | Israel et al. | |
| 5,984,929 A * | 11/1999 | Bashiri et al. | 606/108 |
| 6,027,526 A | 2/2000 | Limon et al. | |
| 6,030,397 A | 2/2000 | Monetti et al. | |
| 6,042,597 A | 3/2000 | Kveen et al. | |
| 6,059,822 A | 5/2000 | Kanesaka et al. | |
| 6,066,149 A | 5/2000 | Samson et al. | |
| 6,066,158 A | 5/2000 | Engelson et al. | |
| 6,106,548 A | 8/2000 | Roubin et al. | |
| 6,146,403 A | 11/2000 | St. Germain | |
| 6,200,335 B1 | 3/2001 | Igaki | |
| 6,206,911 B1 * | 3/2001 | Milo | 623/1.15 |
| 6,217,608 B1 | 4/2001 | Penn et al. | |
| 6,273,910 B1 | 8/2001 | Limon | |
| 6,309,414 B1 | 10/2001 | Rolando et al. | |
| 6,350,271 B1 | 2/2002 | Kurz et al. | |
| 6,398,805 B1 | 6/2002 | Alt | |
| 6,402,431 B1 | 6/2002 | Nish | |
| 6,402,771 B1 | 6/2002 | Palmer et al. | |
| 6,409,754 B1 | 6/2002 | Smith et al. | |
| 6,423,091 B1 | 7/2002 | Hojeibane | |
| 6,468,301 B1 | 10/2002 | Amplatz et al. | |
| 6,475,236 B1 | 11/2002 | Roubin et al. | |
| 6,478,816 B1 | 11/2002 | Kveen et al. | |
| 6,482,217 B1 | 11/2002 | Pintor et al. | |
| 6,488,703 B1 | 12/2002 | Kveen et al. | |
| 6,491,719 B1 | 12/2002 | Fogarty et al. | |
| 6,514,273 B1 | 2/2003 | Voss et al. | |
| 6,551,342 B1 | 4/2003 | Shen et al. | |
| 6,575,995 B1 | 6/2003 | Huter et al. | |
| 6,641,590 B1 | 11/2003 | Palmer et al. | |
| 6,660,021 B1 * | 12/2003 | Palmer et al. | 606/200 |
| 6,679,893 B1 | 1/2004 | Tran | |
| 6,692,504 B2 | 2/2004 | Kurz et al. | |
| 6,706,054 B2 | 3/2004 | Wessman et al. | |
| 6,716,240 B2 | 4/2004 | Fischell et al. | |
| 6,818,013 B2 | 11/2004 | Mitelberg et al. | |
| 6,818,613 B2 | 11/2004 | Sharma et al. | |
| 6,881,222 B2 | 4/2005 | White et al. | |
| 6,949,120 B2 | 9/2005 | Kveen et al. | |
| 6,960,228 B2 | 11/2005 | Mitelberg et al. | |
| 7,008,434 B2 | 3/2006 | Kurz et al. | |
| 7,037,321 B2 | 5/2006 | Sachdeva et al. | |
| 7,037,331 B2 | 5/2006 | Mitelberg et al. | |
| 7,081,130 B2 | 7/2006 | Jang | |
| 7,108,714 B1 | 9/2006 | Becker | |
| 7,195,648 B2 | 3/2007 | Jones et al. | |
| 7,291,166 B2 | 11/2007 | Cheng et al. | |
| 7,300,458 B2 | 11/2007 | Henkes et al. | |
| 7,311,726 B2 | 12/2007 | Mitelberg et al. | |
| 7,316,692 B2 | 1/2008 | Huffmaster | |
| 7,485,130 B2 | 2/2009 | St. Germain | |
| 7,651,513 B2 * | 1/2010 | Teoh et al. | 606/200 |
| 7,655,033 B2 * | 2/2010 | Fearnot et al. | 623/1.15 |
| 7,811,300 B2 | 10/2010 | Feller, III et al. | |
| 7,875,044 B2 | 1/2011 | Feller, III et al. | |
| 7,887,560 B2 | 2/2011 | Kusleika | |
| 2001/0047200 A1 | 11/2001 | White et al. | |
| 2003/0004567 A1 | 1/2003 | Boyle et al. | |
| 2003/0100917 A1 | 5/2003 | Boyle et al. | |
| 2003/0116751 A1 | 6/2003 | Elman | |
| 2003/0176914 A1 | 9/2003 | Rabkin et al. | |
| 2003/0179614 A1 | 9/2003 | Rabkin | |
| 2003/0199921 A1 | 10/2003 | Palmer et al. | |
| 2004/0068314 A1 | 4/2004 | Jones | |
| 2004/0199175 A1 * | 10/2004 | Jaeger et al. | 606/108 |
| 2004/0236368 A1 | 11/2004 | McGuckin et al. | |
| 2005/0209678 A1 | 9/2005 | Henkes et al. | |
| 2005/0267491 A1 | 12/2005 | Kellett et al. | |
| 2006/0116751 A1 | 6/2006 | Bayle et al. | |
| 2006/0265048 A1 | 11/2006 | Cheng et al. | |
| 2006/0287701 A1 | 12/2006 | Pal | |
| 2007/0038178 A1 | 2/2007 | Kusleika | |
| 2007/0191866 A1 | 8/2007 | Zart et al. | |
| 2007/0198051 A1 | 8/2007 | Clubb et al. | |
| 2007/0225739 A1 | 9/2007 | Pintor et al. | |
| 2007/0280367 A1 | 12/2007 | Nakao et al. | |
| 2007/0288054 A1 | 12/2007 | Tanaka et al. | |
| 2008/0125855 A1 | 5/2008 | Henkes et al. | |
| 2008/0208244 A1 | 8/2008 | Boylan et al. | |
| 2008/0262487 A1 | 10/2008 | Wensel et al. | |
| 2009/0105722 A1 | 4/2009 | Fulkerson et al. | |
| 2009/0105737 A1 | 4/2009 | Fulkerson et al. | |
| 2010/0100106 A1 | 4/2010 | Ferrera | |
| 2010/0114135 A1 | 5/2010 | Wilson et al. | |
| 2010/0161034 A1 | 6/2010 | Leanna et al. | |
| 2010/0174309 A1 | 7/2010 | Fulkerson et al. | |
| 2010/0318097 A1 | 12/2010 | Ferrera et al. | |
| 2010/0331853 A1 | 12/2010 | Garcia et al. | |
| 2011/0009950 A1 | 1/2011 | Grandfield et al. | |
| 2011/0130784 A1 | 6/2011 | Kusleika | |

FOREIGN PATENT DOCUMENTS

| | | |
|---|---|---|
| DE | 4032759 A1 | 4/1992 |
| DE | 19834956 A1 | 5/1999 |
| DE | 10233085 A1 | 1/2004 |
| DE | 10301850 A1 | 1/2004 |
| DE | 10301850 A1 | 7/2004 |
| EP | 0897698 A2 | 2/1999 |
| EP | 0914807 A2 | 5/1999 |
| EP | 0916362 A1 | 5/1999 |
| EP | 1266640 A2 | 12/2002 |
| EP | 1362564 A1 | 11/2003 |
| EP | 1266640 A3 | 1/2004 |
| EP | 1266640 B1 | 8/2007 |
| EP | 1534178 B1 | 10/2007 |
| EP | 1351626 B1 | 2/2008 |
| EP | 1542617 B1 | 1/2011 |
| GB | 2463592 B | 8/2010 |
| JP | 62049841 A | 3/1987 |
| JP | 7124251 A | 5/1995 |
| JP | 2010264261 A | 11/2010 |
| WO | 9704711 A1 | 2/1997 |
| WO | 9725000 A1 | 7/1997 |
| WO | 0145592 A1 | 6/2001 |
| WO | WO0145592 A1 | 6/2001 |
| WO | 2004006804 A1 | 1/2004 |
| WO | 2004008991 A1 | 1/2004 |
| WO | 2008063156 A2 | 5/2008 |
| WO | 2010010545 A1 | 1/2010 |

OTHER PUBLICATIONS

EV3, Fully Deployable. Completely Retrievable. Solitaire AB Neurovascular Remodeling Device, Solitaire AB Brochure, www.ev3.net, accessed on Jul. 16, 2009.

International Search Report and Written Opinion for PCT International Application No. PCT/US2010/041434 issued by the ISA dated Sep. 8, 2010.

Wilson, Scott et al., Devices and Methods for Temporarily Opening a Blood Vessel, U.S. Patent Application, Oct. 31, 2008.

International Search Report and Written Opinion for PCT International Application No. PCT/US2012/023858 issued by the ISA dated Jun. 4, 2012.

PCT International Preliminary Report on Patentability for PCT/US2010/041434, issued Jan. 10, 2012, IB of WIPO, Geneva Switzerland, containing the written opinion of the US Patent Office for PCT/US2010/041434, issued Sep. 8, 2010, Alexandria, VA, USA.

* cited by examiner

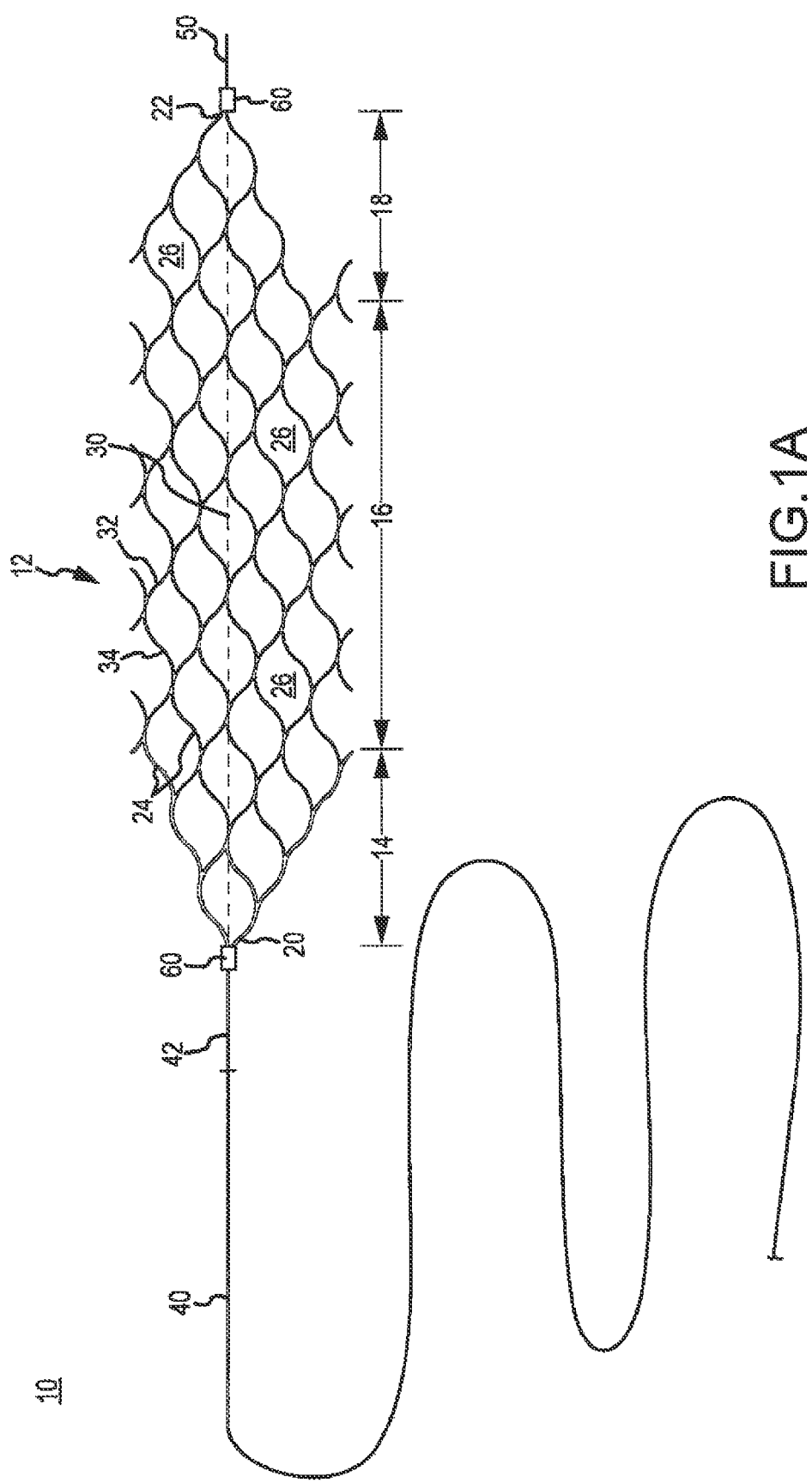

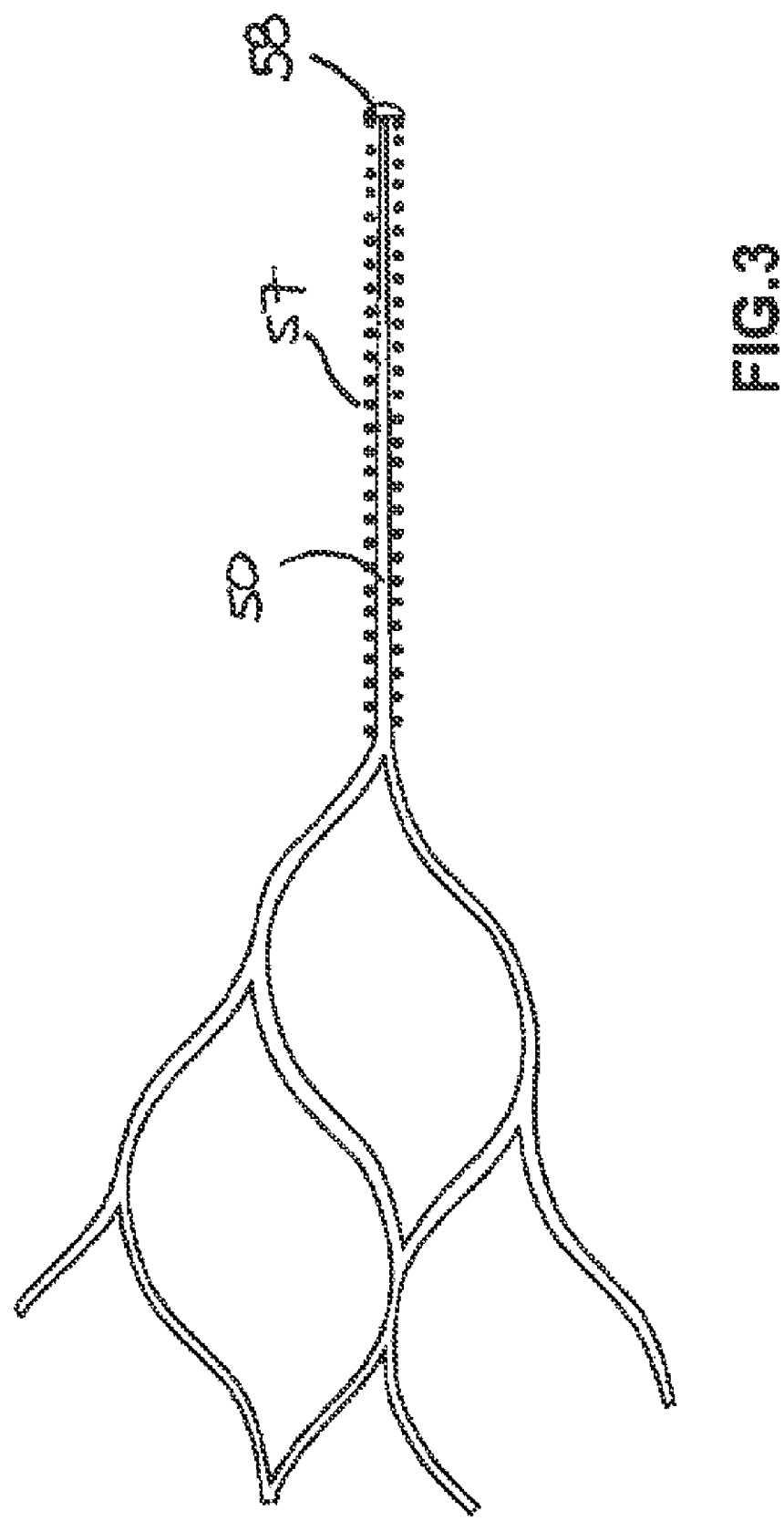

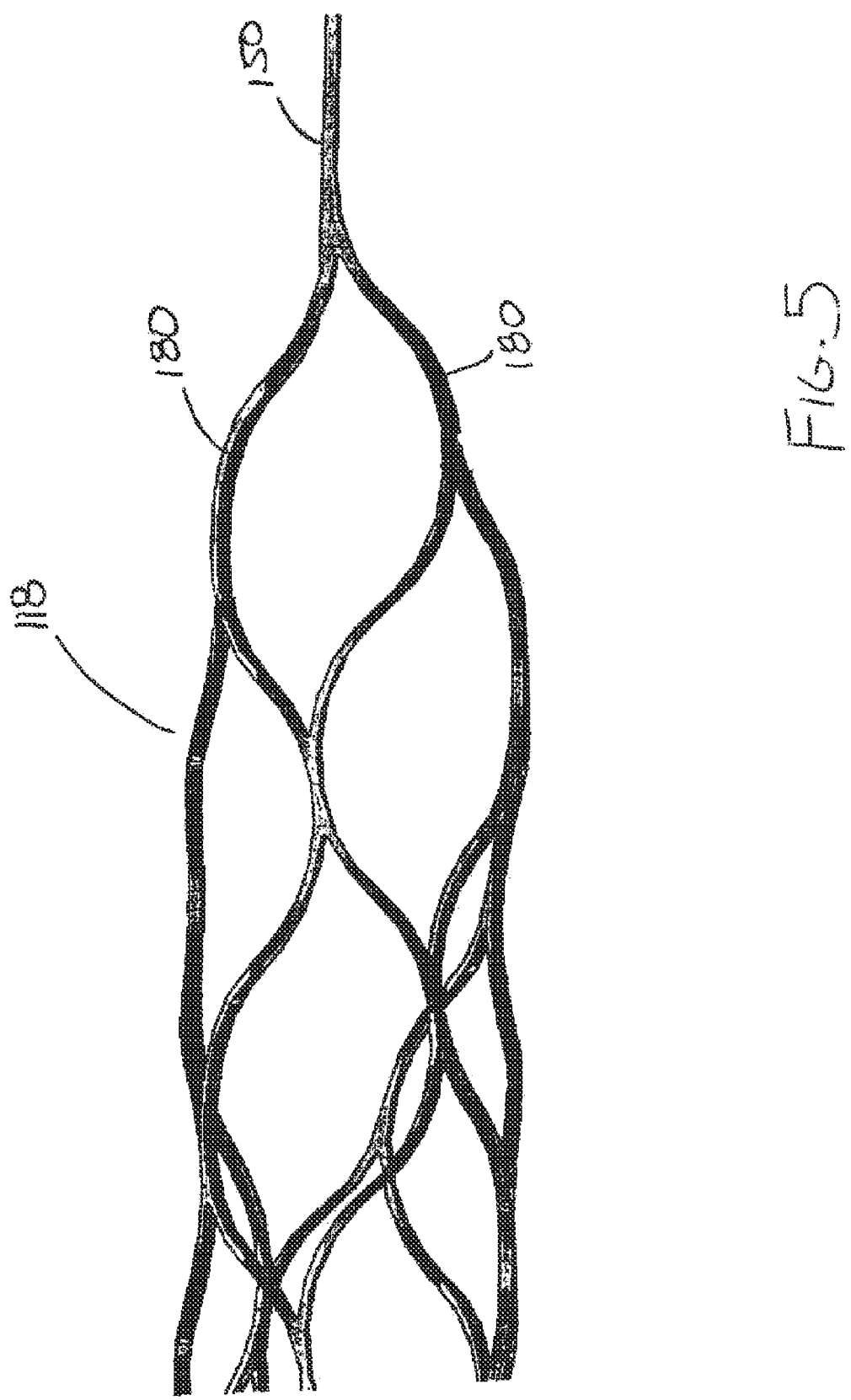

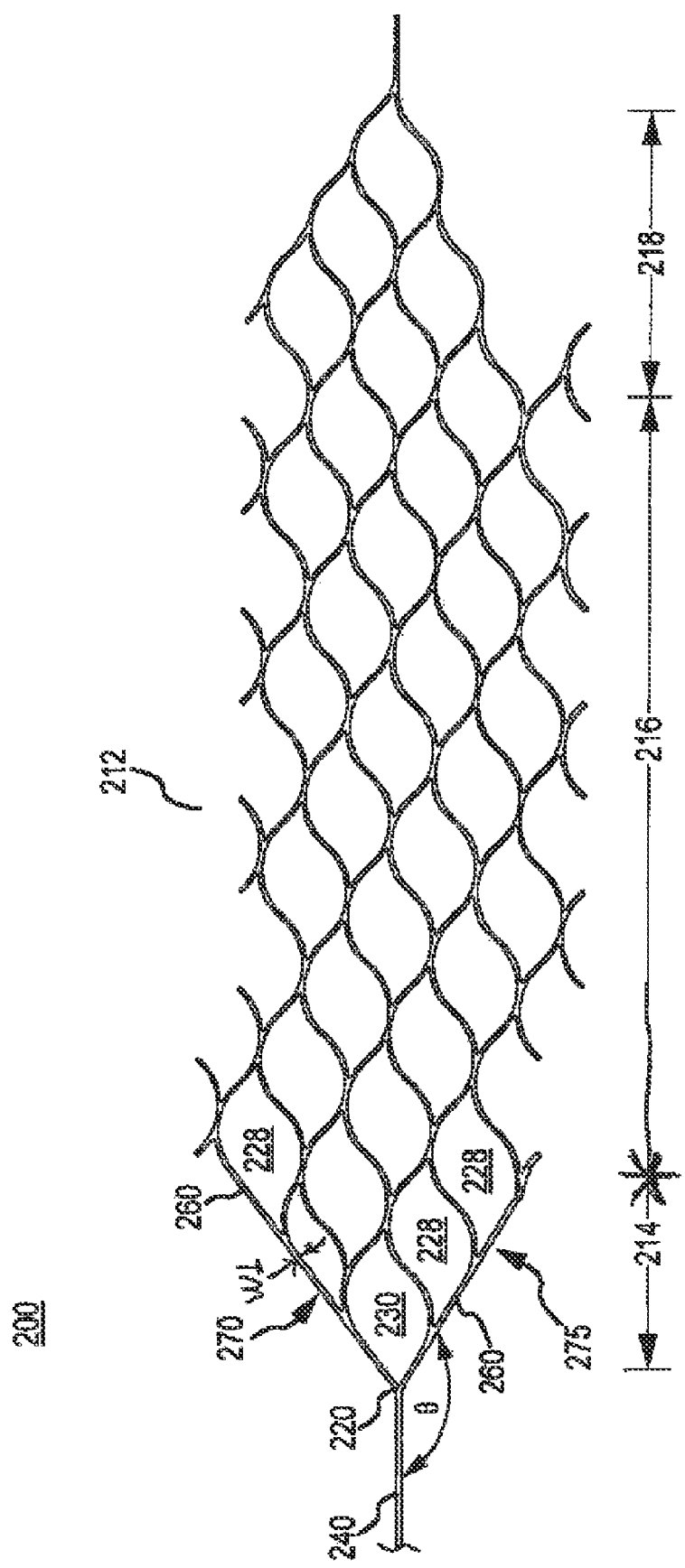

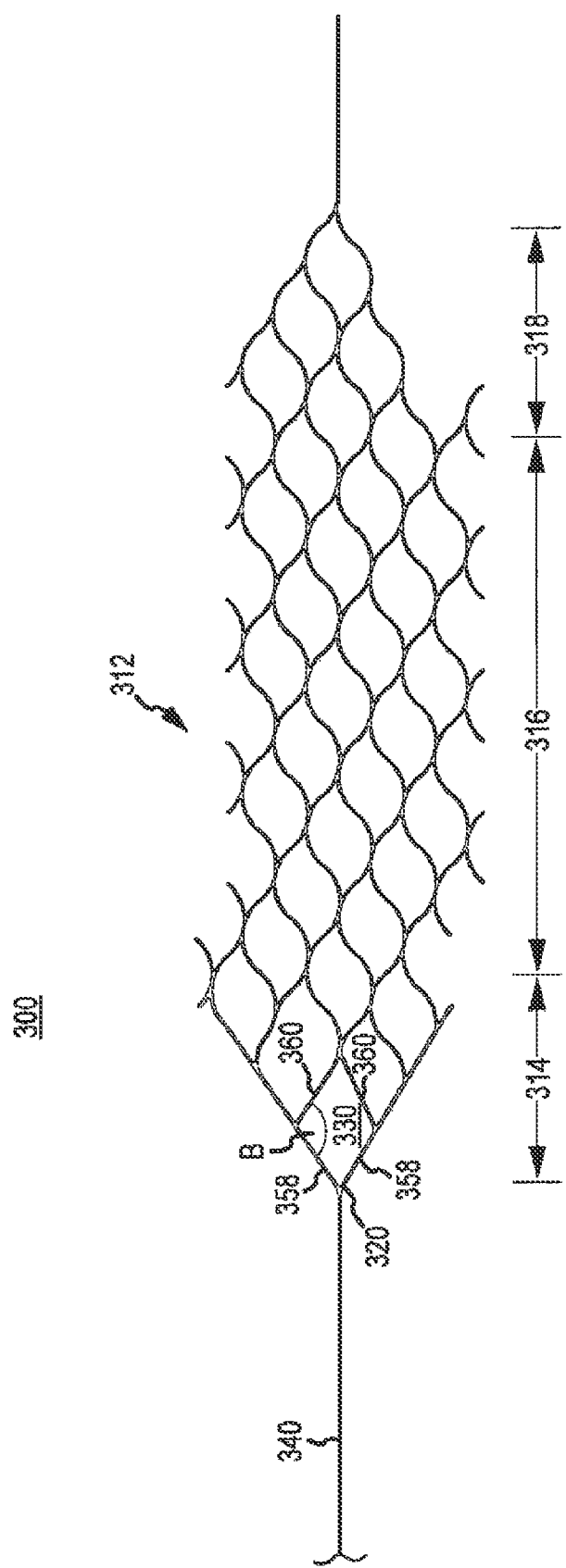

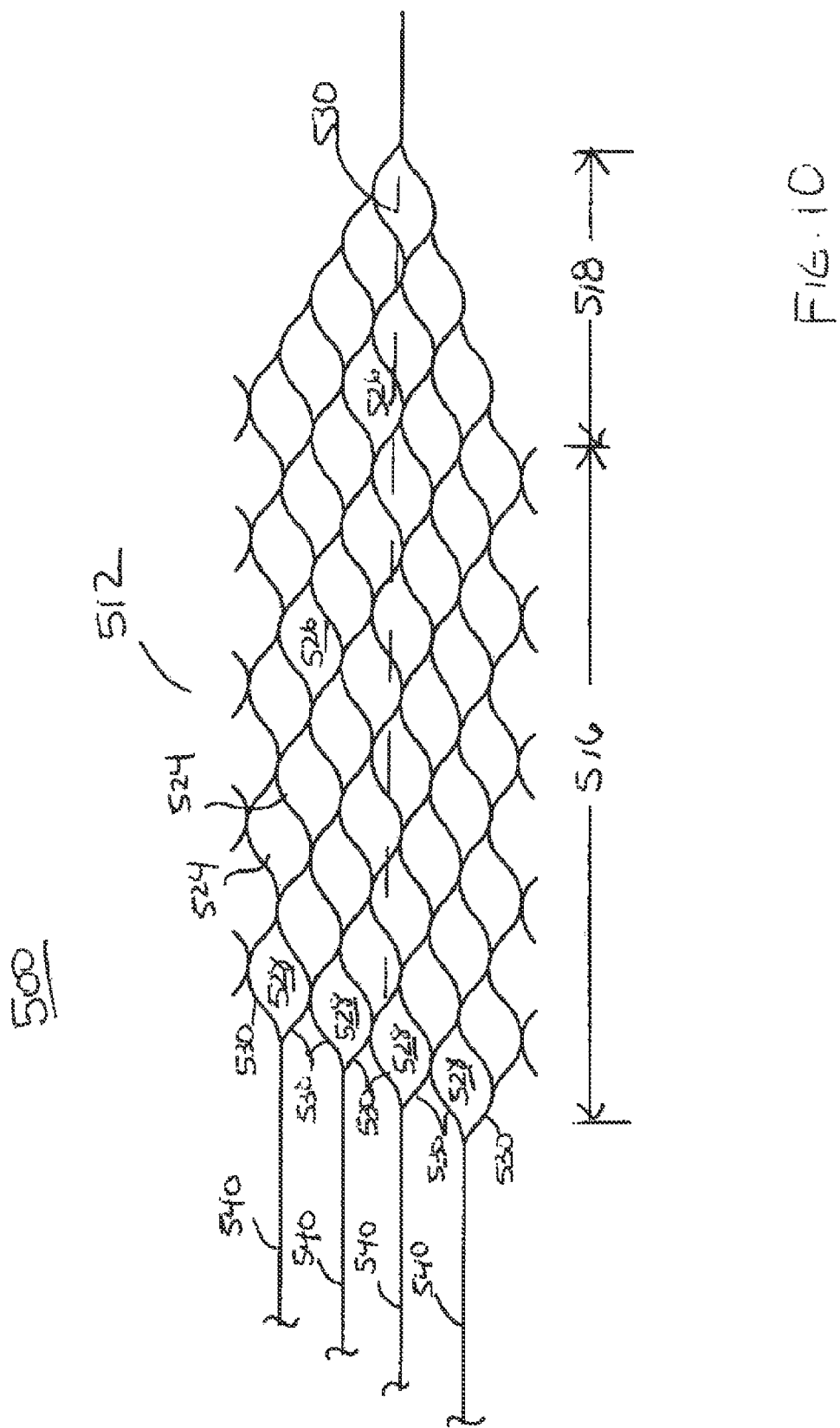

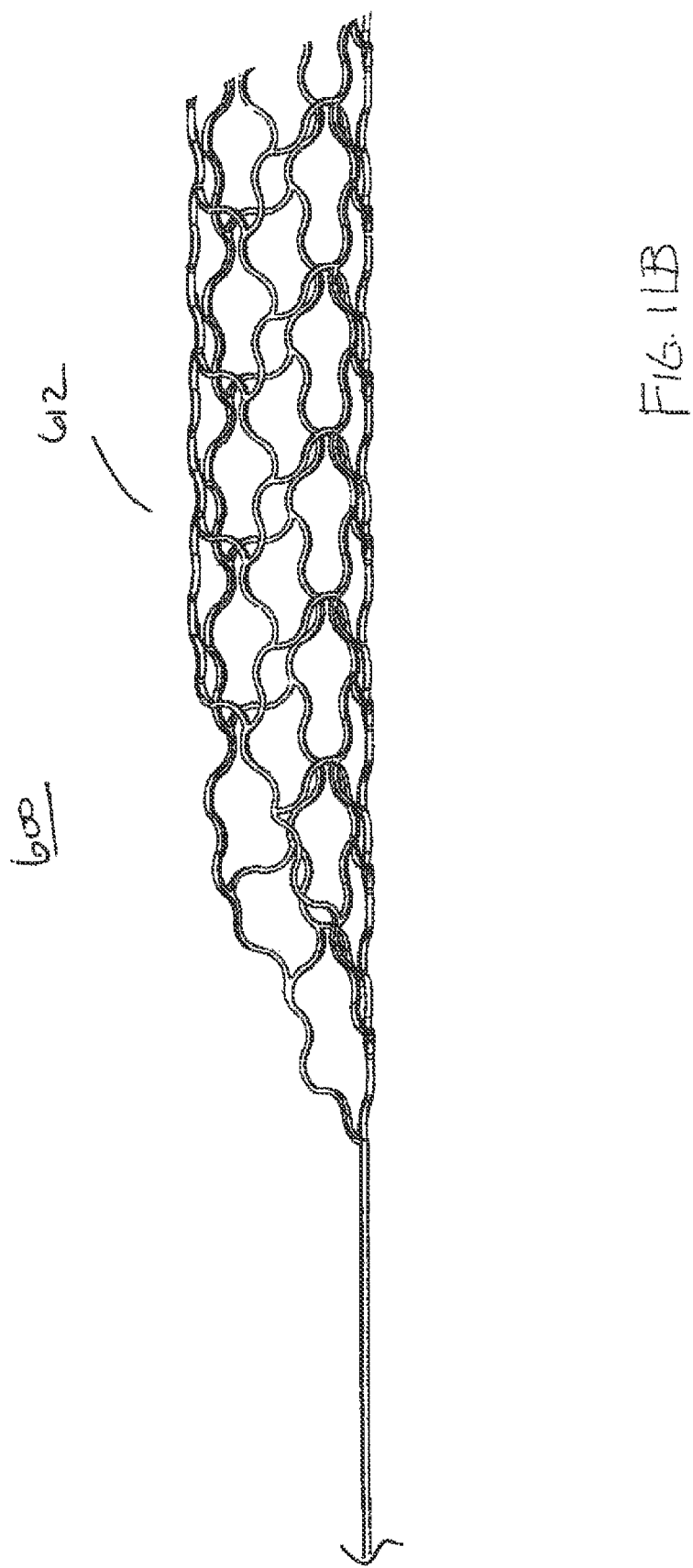

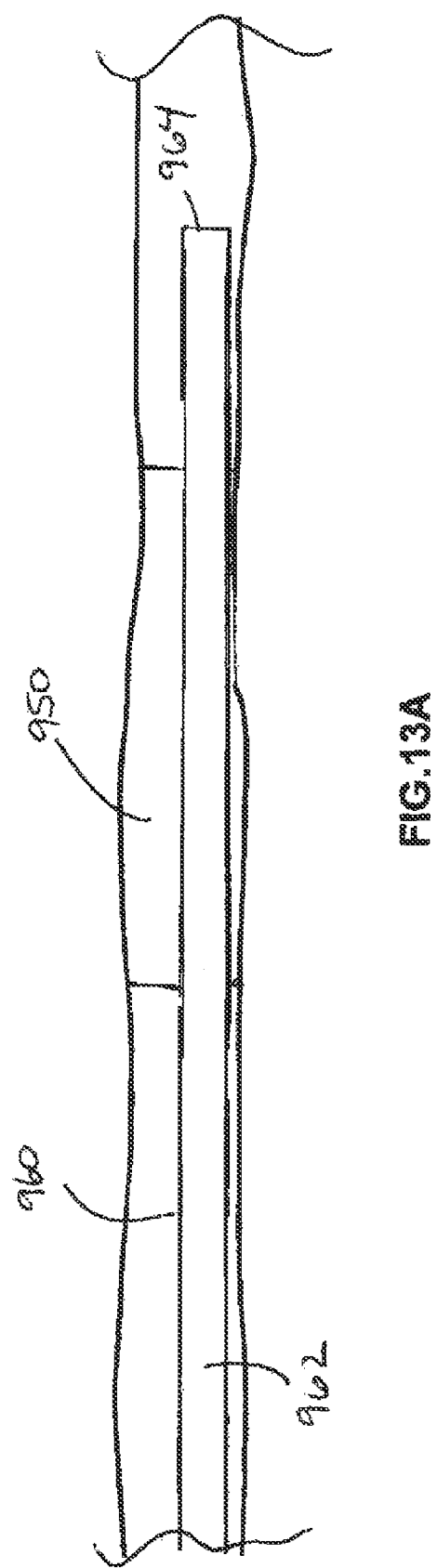

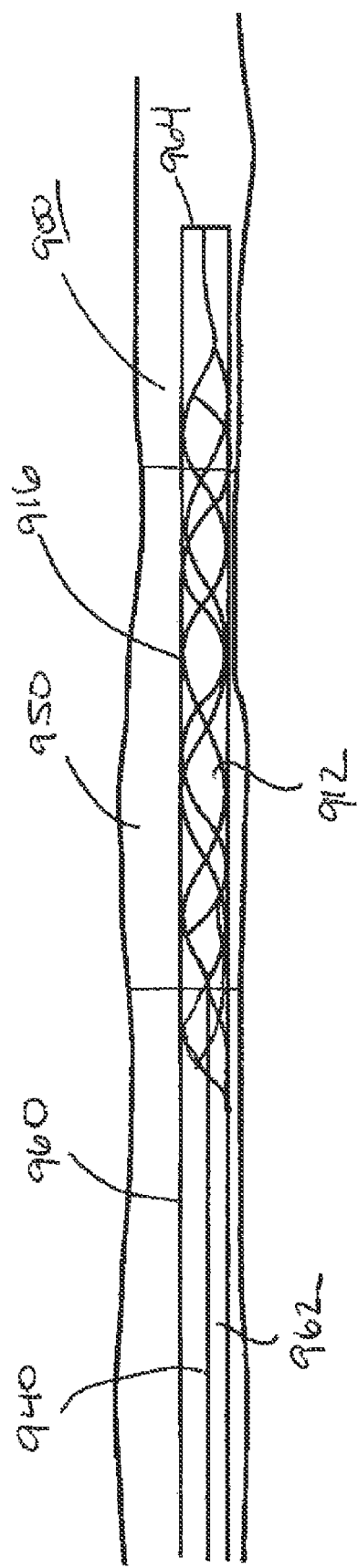

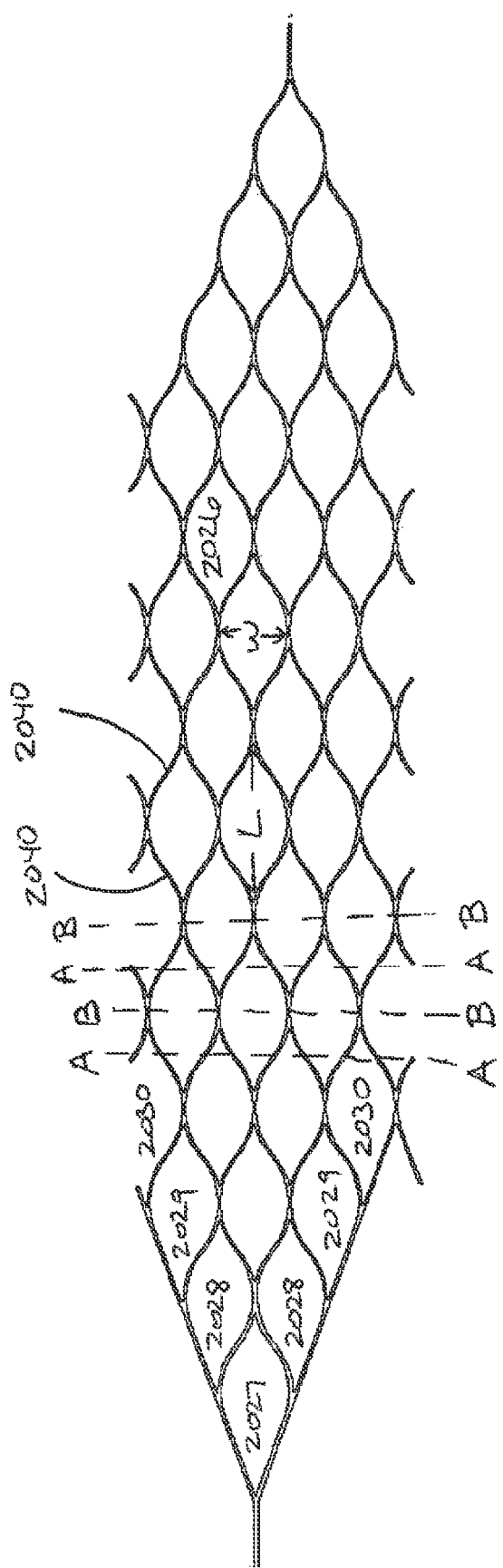

VASCULAR AND BODILY DUCT TREATMENT DEVICES AND METHODS

RELATED APPLICATION

This application claims the benefit to and is a continuation-in-part of U.S. patent application Ser. No. 12/643,942, filed Dec. 21, 2009, which is a continuation-in-part of U.S. patent application Ser. No. 12/573,676, filed Oct. 5, 2009, which is a continuation-in-part of U.S. patent application Ser. No. 12/499,713, filed Jul. 8, 2009.

TECHNICAL FIELD

This application relates to devices and methods for treating the vasculature and other ducts within the body.

BACKGROUND

Self-expanding prostheses, such as stents, covered stents, vascular grafts, flow diverters, and the like have been developed to treat ducts within the body. Many of the prostheses have been developed to treat blockages within the vasculature and also aneurysms that occur in the brain. What are needed are improved treatment methods and devices for treating the vasculature and other body ducts, such as, for example, aneurysms, stenoses, embolic obstructions, and the like.

SUMMARY OF THE DISCLOSURE

In accordance with one implementation a vascular or bodily duct treatment device is provided that comprises an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within the bodily duct or vasculature of a patient, the expandable member comprising a plurality of cell structures, the expandable member having a proximal end portion with a proximal end, a cylindrical main body portion and a distal end portion with a distal end, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that, in a two-dimensional view, form first and second substantially linear rail segments that each extend from a position at or near the proximal-most end of the expandable member to a distal position at or near the cylindrical main body portion. In one implementation the self-expandable member has a longitudinal slit extending along at least a portion of the length of the self-expandable member between the proximal end and the distal end.

In accordance with another implementation a kit is provided that comprises an elongate flexible wire having a proximal end and a distal end with an elongate self-expandable member coupled to the distal end, the self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment in the bodily duct or vasculature of a patient, the self-expandable member comprising a plurality of cell structures, the self-expandable member having a proximal end portion with a proximal end, a cylindrical main body portion and a distal end portion with a distal end, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that, in a two-dimensional view, form first and second substantially linear rail segments that each extend from a position at or near the proximal-most end of the expandable member to a distal position at or near the cylindrical main body portion, the elongate wire with the expandable member having a first length; and a delivery catheter having a second length and sufficient flexibility to navigate the vasculature or bodily duct of the patient, the delivery catheter having a proximal end, a distal end and an inner lumen, the inner lumen having a diameter sufficient to receive the self-expandable member in its unexpanded position and for advancing the unexpanded member from the proximal end to the distal end of the catheter, the second length being less than the first length to allow distal advancement of the self-expandable member beyond the distal end of the catheter to permit the expandable member to deploy toward its expanded position, the distal end of the catheter and the self-expandable member configured to permit proximal retraction of the self-expandable member into the lumen of the catheter when the self-expandable member is partially or fully deployed outside the distal end of the catheter. In one implementation, the self-expandable member has a longitudinal slit extending along at least a portion of the length of the self-expandable member between the proximal end and the distal end.

In accordance with one implementation, a bodily duct or vascular treatment device is provided having an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within the bodily duct or vasculature of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that, in a two-dimensional view, form first and second substantially linear rail segments that each extend from a position at or near the proximal-most end of the expandable member to a position at or near the cylindrical main body portion. In one implementation, connected to the proximal-most end of the expandable member is a proximally extending elongate flexible wire having a length and flexibility sufficient for navigating and accessing the vasculature or bodily duct of the patient.

In accordance with another implementation, a vascular treatment device is provided that includes an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within the vasculature of a patient, the expandable member comprising a plurality of generally longitudinal undulating elements with adjacent undulating elements being interconnected in a manner to form a plurality of cell structures that are arranged to induce twisting of the expandable member as the expandable member transitions from the unexpanded position to the expanded position, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that form first and second substantially linear rail segments that each extend from a position at or near the proximal-most end of the expandable member to a position at or near the cylindrical main body portion. In one implementation, connected to the proximal-most end of the expandable member is a proximally extending elongate flexible wire having a length and flexibility sufficient for navigating and accessing the vasculature or bodily duct of the patient.

In accordance with another implementation, a bodily duct or vascular treatment device is provided that includes an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within the bodily duct or vasculature of a patient, the expandable member comprising a plurality of generally longitudinal undulating elements with adjacent undulating elements being interconnected to form a plurality of diagonally disposed cell structures, the expandable member having a cylindrical portion and a distal end portion, the cell structures in the cylindrical portion extending circumferentially around a longitudinal axis of the expandable member, the cell structures in the distal end portion extending less than circumferentially around the longitudinal axis of the expandable member, the proximal-most cell structures in the main body portion having proximal-most end points. One or more of the proximal-most end points of the expandable member have a proximally extending elongate flexible wire having a length and flexibility sufficient for navigating and accessing the vasculature or bodily duct of the patient.

In accordance with another implementation, a kit is provided that includes an elongate flexible wire having a proximal end and a distal end with an elongate self-expandable member attached to the distal end, the self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within a bodily duct or vasculature of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer-most cell structures in the proximal end portion having proximal-most linear wall segments that, in a two-dimensional view, form first and second substantially linear rail segments that each extend from a position at or near the proximal-most end of the expandable member to a position at or near the cylindrical main body portion, the elongate wire and expandable member having a first length, and a delivery catheter having a second length and sufficient flexibility to navigate the vasculature or bodily duct of a patient, the delivery catheter having a proximal end, a distal end and an inner diameter, the inner diameter sufficient to receive the expandable member in its unexpanded position and for advancing the unexpanded member from the proximal end to the distal end of the catheter, the second length being less that the first length to allow distal advancement of the expandable member beyond the distal end of the catheter to permit the expandable member to deploy toward its expanded position, the distal end of the catheter and the expandable member configured to permit proximal retraction of the expandable member into the catheter when the expandable member is partially or fully deployed outside the distal end of the catheter.

In accordance with another implementation, a method for removing an embolic obstruction from a vessel of a patient is provided that includes (a) advancing a delivery catheter having an inner lumen with proximal end and a distal end to the site of an embolic obstruction in the intracranial vasculature of a patient so that the distal end of the inner lumen is positioned distal to the embolic obstruction, the inner lumen having a first length, (b) introducing an embolic obstruction retrieval device comprising an elongate flexible wire having a proximal end and a distal end with an elongate self-expandable member attached to the distal end into the proximal end of the inner lumen of the catheter and advancing the self-expandable member to the distal end of the lumen, the self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within an embolic obstruction of a patient, the expandable member comprising a plurality of generally longitudinal undulating elements with adjacent undulating elements being interconnected in a manner to form a plurality of cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the outer cell structures in the proximal end portion having proximal linear wall segments that, in a two-dimensional view, form first and second substantially linear rail segments that each extend from a position at or near the proximal end of the expandable member to a position at or near the cylindrical main body portion, the elongate wire and expandable member in combination having a second length longer than the first length, (c) proximally retracting the delivery catheter sufficient to deploy the self-expandable device so that the one or more of the cell structures entrap at least a portion of the embolic obstruction, and (d) proximally retracting the delivery catheter and self-expandable device to outside the patient. In an alternative implementation, the self-expandable member is partially or fully retracted into the inner lumen of the delivery catheter prior to proximally retracting the delivery catheter and self-expandable device to outside the patient.

In accordance with another implementation, a device is provided comprising an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within a vessel or duct of a patient, the expandable member comprising a plurality of cell structures, the expandable member having a proximal end portion with a proximal end and a cylindrical main body portion, the cell structures in the main body portion comprise a first plurality of intersecting struts and extend circumferentially around a longitudinal axis of the expandable member, the cell structures in the proximal end portion comprise a second plurality of intersecting struts and extend less than circumferentially around the longitudinal axis of the expandable member, at least some of the first plurality of intersecting struts having a thickness to width ratio of greater than one.

In accordance with yet another implementation, a device is provided comprising a delivery wire, an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within a vessel or duct of a patient, the expandable member comprising a plurality of cell structures, the expandable member having a proximal end portion with a proximal end and a cylindrical main body portion, the proximal end having an integrally formed wire segment extending therefrom with a coil positioned about the wire segment, the coil comprising a first closely wound segment and a second loosely wound segment that contains at least one gap, the cell structures in the main body portion extending circumferentially around a longitudinal axis of the expandable member, the cell structures in the proximal end portion extending less than circumferentially around the longitudinal axis of the expandable member, a proximal end of the wire segment attached to a distal end of the delivery wire by a bonding agent within the second loosely wound segment of the coil.

In accordance with yet another implementation, a device is provided comprising an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within a vessel or duct of a patient, the expandable member comprising a plurality of cell structures, the expandable member having a proximal end portion with a proximal end and a cylindrical main body portion, the cell structures in the main body portion extending circumferentially around a longitudinal axis of the expandable member, the cell structures in the proximal end portion extending less than circumferentially around the longitudinal axis of the expandable member, the cell structures having dimensional and material characteristics that result in about a −1.5N to a about a −3.5N overall reduction in radial force along the length of the expandable member per millimeter of expansion during about an initial 0.50 mm diametric range of expansion from the nominal diameter and that results in about a −0.10N to about a −0.50N overall reduction in radial force along the length of the expandable member per millimeter of expansion during subsequent diametric ranges of expansion. In one implementation the elongate self-expandable member has a designated maximum second nominal diameter, the radial force exerted by the elongate self-expandable member being greater than zero when expanded to the maximum second nominal diameter.

In accordance with yet another implementation, a device is provided comprising an elongate self-expandable member movable from a first delivery position to a second placement position, in the first delivery position the expandable member being in an unexpanded position and having a nominal first diameter and in the second position the expandable member being in a radially expanded position and having a second nominal diameter greater than the first nominal diameter for deployment within the bodily duct or vasculature of a patient, the expandable member comprising a plurality of generally longitudinal undulating elements with adjacent undulating elements being interconnected in a manner to form a plurality of diagonally disposed cell structures, the expandable member having a proximal end portion, a cylindrical main body portion and a distal end portion, the cell structures in the main body portion extending circumferentially around a longitudinal axis of the expandable member, the cell structures in the proximal and distal end portions extending less than circumferentially around the longitudinal axis of the expandable member, the cell structures in the proximal end portion extending less than circumferentially around the longitudinal axis of the expandable member, the cell structures having dimensional and material characteristics that result in about a −1.5N to a about a −3.5N overall reduction in radial force along the length of the expandable member per millimeter of expansion during about an initial 0.50 mm diametric range of expansion from the first nominal diameter and that results in about a −0.10N to about a −0.50N overall reduction in radial force along the length of the expandable member per millimeter of expansion during subsequent diametric ranges of expansion. In one implementation the elongate self-expandable member has a designated maximum second nominal diameter, the radial force exerted by the elongate self-expandable member being greater than zero when expanded to the maximum second nominal diameter.

BRIEF DESCRIPTION OF THE DRAWINGS

Alternative implementations of the present disclosure are described herein with reference to the drawings wherein:

FIG. 1A illustrates a two-dimensional plane view of an expandable member of a treatment device in one embodiment.

FIG. 3 illustrates the distal end of an expandable member having an atraumatic tip.

FIG. 5 illustrates a distal end of an expandable member in one embodiment.

FIG. 6A illustrates a two-dimensional plane view of an expandable member of a treatment device in another embodiment.

FIG. 7A illustrates a two-dimensional plane view of an expandable member of a treatment device in another embodiment.

FIG. 10 illustrates a two-dimensional plane view of an expandable member of a treatment device in another embodiment.

FIG. 11B is an isometric view of the expandable member illustrated in FIG. 11A.

FIGS. 13A through 13C illustrate a method for retrieving an embolic obstruction in accordance with one implementation.

FIG. 24A illustrates a two-dimensional plane view of an expandable member of a treatment device in yet another embodiment.

DETAILED DESCRIPTION

Figure 1B:
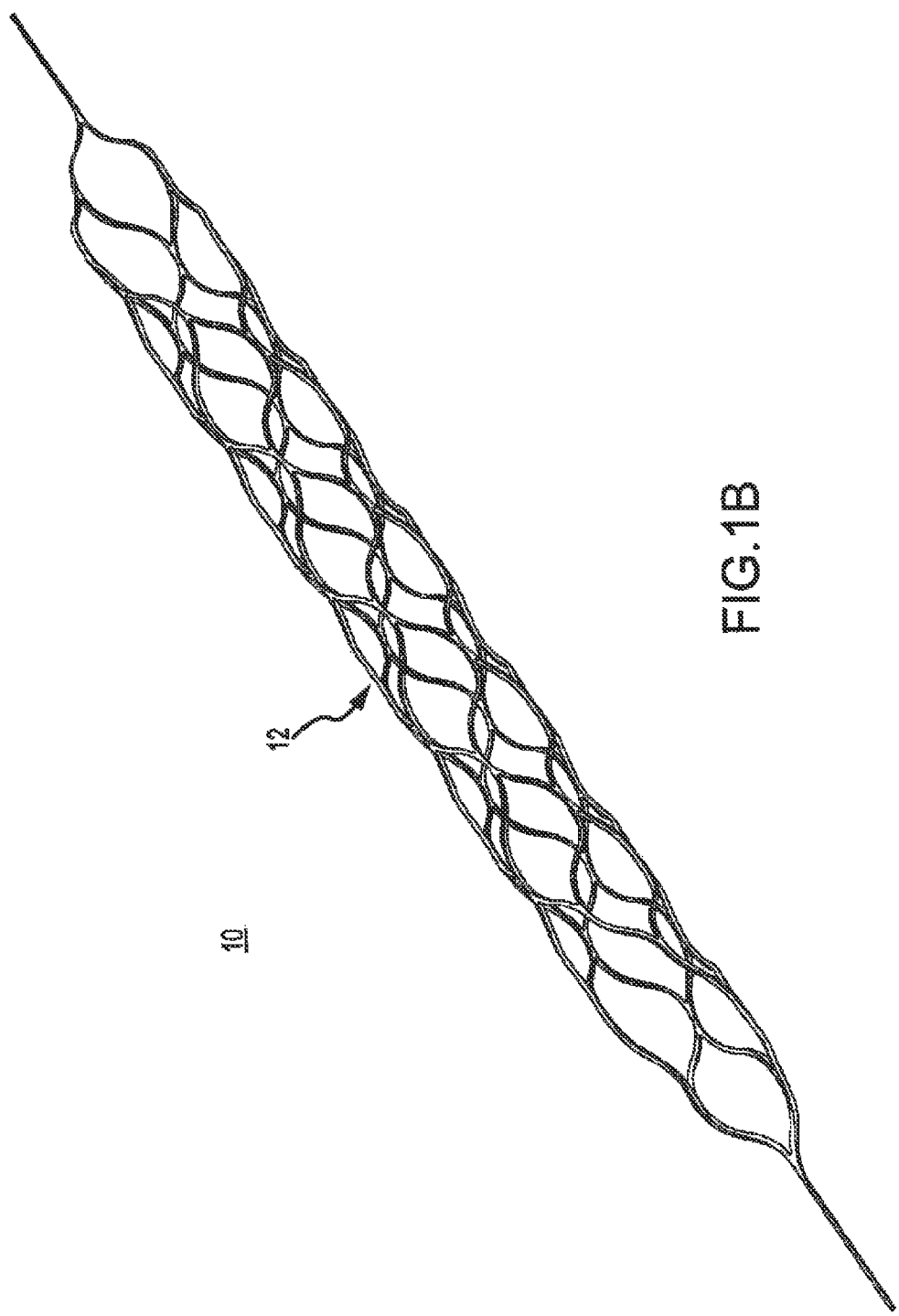
FIG. 1B is an isometric view of the expandable member illustrated in FIG. 1A

FIGS. 1A and 1B illustrate a vascular or bodily duct treatment device 10 in accordance with one embodiment of the present invention. Device 10 is particularly suited for accessing and treating the intracranial vascular of a patient, such as for example treating aneurysms or capturing and removing embolic obstructions. It is appreciated however, that device 10 may be used for accessing and treating other locations within the vasculature and also other bodily ducts. Other uses include, for example, treating stenoses and other types of vascular diseases and abnormalities. FIG. 1A depicts device 10 in a two-dimensional plane view as if the device were cut and laid flat on a surface. FIG. 1B depicts the device in its manufactured and/or expanded tubular configuration. Device 10 includes a self-expandable member 12 that is attached or otherwise coupled to an elongate flexible wire 40 that extends proximally from the expandable member 12. In one embodiment, the expandable member 12 is made of shape memory material, such as Nitinol, and is preferably laser cut from a tube. In one embodiment, the expandable member 12 has an integrally formed proximally extending wire segment 42 that is used to join the elongate flexible wire 40 to the expandable member 12. In such an embodiment, flexible wire 40 may be joined to wire segment 42 by the use of solder, a weld, an adhesive, or other known attachment method. In an alternative embodiment, the distal end of flexible wire 40 is attached directly to a proximal end 20 of the expandable member 12. In one embodiment, the distal end of wire 40 has a flat profile with a width of about 0.005 inches with the width and thickness of the wire segment 42 being about 0.0063 and about 0.0035 inches, respectively.

Figure 25:
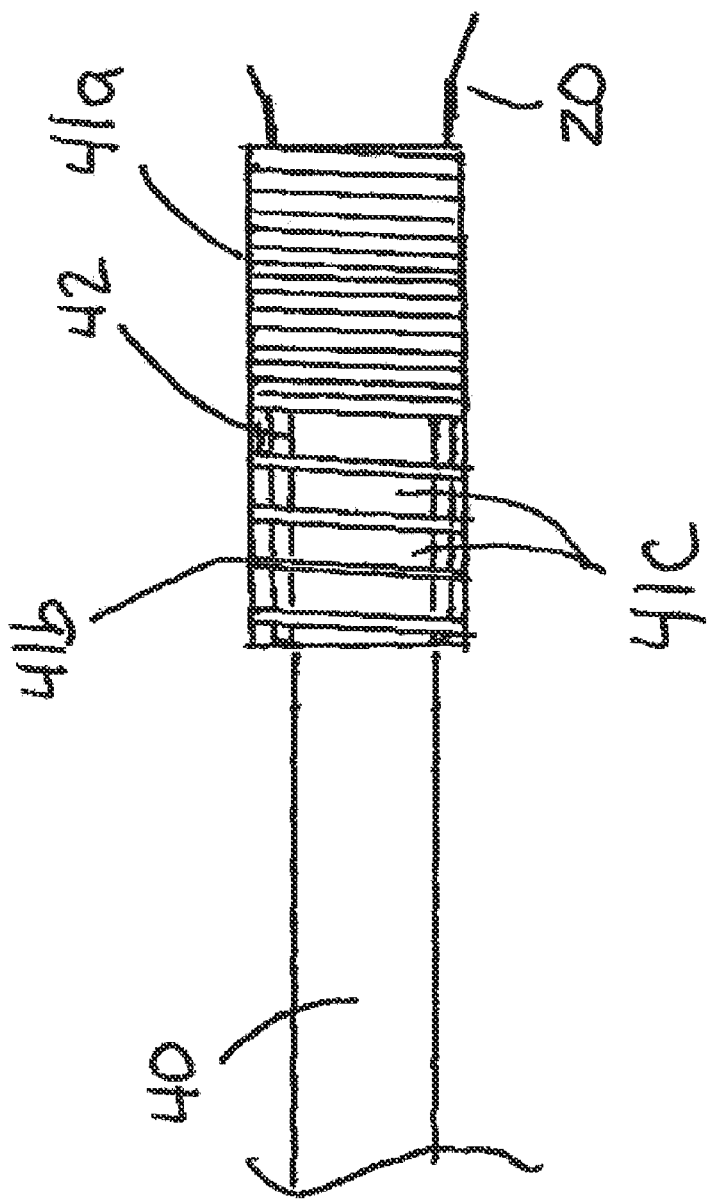
FIG. 25 illustrates a manner in which the proximal extending wire segment of an expandable device is attached to a delivery wire in one embodiment.

In one embodiment, the distal end of wire 40 is attached to the proximally extending wire segment 42 by the following method, resulting in the joint illustrated in FIG. 25. In one implementation, a coil 41 is positioned over wire segment 42, the coil having a closely wrapped segment 41a abutting the proximal end of expandable member 12, and a loosely wrapped segment 41b that includes one or more gaps 41c. The size of the one or more gaps 41c being sufficient to introduce a bonding agent into at least the inner cavity of coil segment 41b. In one embodiment, the length of wire segment 42 and the coil 41 are equal. In one embodiment the length of the wire segment 42 is 4.0 millimeters with the coil 41 being of equal length. Once the coil 41 has been placed over the wire segment 42, the distal end of wire 40 is placed within coil segment 41b so that it makes contact with and overlaps the proximal end portion of wire segment 42. A bonding agent is then applied through the gaps 41*c* of coil 41 to bond the wire 40 with wire segment 41. The bonding agent may be an adhesive, solder, or any other suitable bonding agent. When the bonding agent is a solder, a preceding step in the process involves coating the distal end portion of wire 40 and the proximal end portion of wire segment 42 with tin or another suitable wetting agent. In one implementation the solder is gold and is used to enhance the radiopacity of the joint so that the joint may serve as a proximal radiopaque marker. In addition to the use of gold, all or portions of the coil may be made of a radiopaque material to further enhance the radiopacity of the joint. According to one embodiment, the length of overlap between the wire 40 and wire segment 42 is between 0.75 and 1.0 millimeters. In the same implementation or in other implementations, the length of coil segment 41*b* is equal, or substantially equal, to the overlap length of the wire 40 and wire segment 42. In an alternative embodiment, in lieu of the use of a single coil 41, two or more coils in abutting relationship are used with, for example, a first closely wound coil abutting the proximal end 20 of the expandable member 12 and a second loosely wound coil with gaps situated proximal to the closely wound coil. Although not shown in the figures, in one embodiment a distal end length of wire 40 is tapers in the distal direction from a nominal diameter to a reduced profile. Along this length is provided a distal wire coil of a constant outer diameter with no taper. In accordance with one implementation, the diameter of coil 41 has the same outer diameter as the distal wire coil.

One advantage of the joint construction is that it is resistant to buckling while the device is being pushed through a delivery catheter while at the same time being sufficiently flexible to enable the device to be delivered through the tortuous anatomy of a patient. In addition, the joint is able to withstand high tensile and torque loads without breaking. Load test have shown the joint of the previously described embodiment can withstand in excess of 2 pounds of tensile stress. In one embodiment, coil 41 is made of a radiopaque material to also function as a proximal radiopaque marker.

Figure 28A:
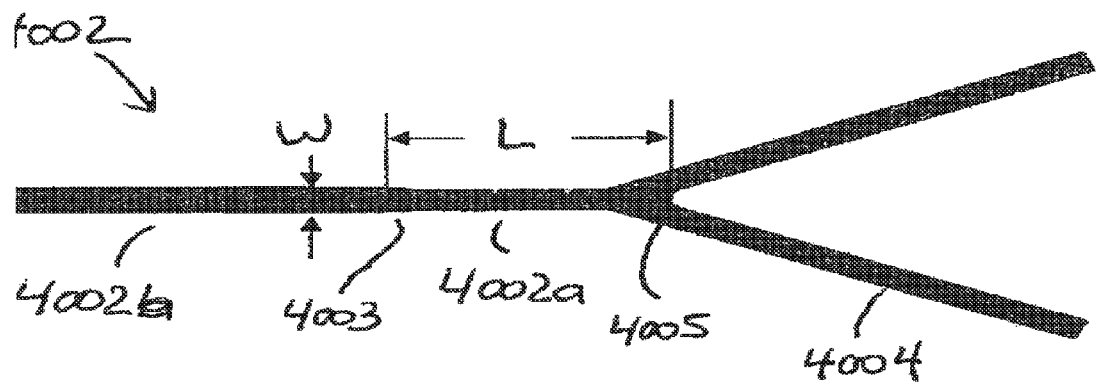
FIGS. 28A and 28B illustrate a proximal wire segment and a distal wire segment, respectively, of an expandable member in one implementation.

FIG. 28A depicts an alternative proximal wire segment construction. As shown, the proximal wire segment 4002 comprises a first section 4002*a* and a second section 4002*b*, with the second section 4002*b* having a width W greater than the width of the first section. In one implementation a tapered transition section 4003 joins the first and second sections 4002*a* and 4002*b*. In one implementation the width of the first section 4002*a* is about 0.0063 inches while the width W of the second section is between about 0.0085 inches and about 0.0105 inches. In one implementation the length L between the proximal end 4005 of the expandable member 4004 and second section 4002*b* of the wire segment 4002 is between about 0.017 inches and about 0.022 inches. An advantage of the inclusion of the second section 4002*b* is that the greater width dimension provides a larger surface area for bonding the wire segment 4002 to the elongate wire 40 used in the delivery and refraction of the elongate member from a duct of a patient. In one implementation the first section 4002*a* has a circular or substantially circular construction and the second section 4002*b* has a flat profile formed by a pressing/coining operation.

In the embodiment of FIGS. 1A and 1B, expandable member 12 includes a plurality of generally longitudinal undulating elements 24 with adjacent undulating elements being out-of-phase with one another and connected in a manner to form a plurality of diagonally disposed cell structures 26. The expandable member 12 includes a proximal end portion 14, a cylindrical main body portion 16 and a distal end portion 18 with the cell structures 26 in the main body portion 16 extending continuously and circumferentially around a longitudinal axis 30 of the expandable member 12. The cell structures 26 in the proximal end portion 14 and distal end portion 18 extend less than circumferentially around the longitudinal axis 30 of the expandable member 12.

In one embodiment, expandable member 12 has an overall length of about 33.0 millimeters with the main body portion 16 measuring about 16.0 millimeters in length and the proximal and distal end portions 14 and 18 each measuring about 7.0 millimeters in length. In alternative embodiments, the length of the main body portion 16 is generally between about 2.5 to about 3.5 times greater than the length of the proximal and distal end portions 14 and 18.

In use, expandable member 12 is advanced through the tortuous vascular anatomy or bodily duct of a patient to a treatment site in an unexpanded or compressed state (not shown) of a first nominal diameter and is movable from the unexpanded state to a radially expanded state of a second nominal diameter greater than the first nominal diameter for deployment at the treatment site. In alternative exemplary embodiments the first nominal diameter (e.g., average diameter of main body portion 16) ranges between about 0.017 to about 0.030 inches, whereas the second nominal diameter (e.g., average diameter of main body portion 16) is between about 2.5 to about 5.0 millimeters. In one implementation, the dimensional and material characteristics of the cell structures 26 residing in the main body portion 16 of the expandable material 12 are selected to produce sufficient radial force and contact interaction to cause the cell structures 26 to engage with an embolic obstruction residing in the vascular in a manner that permits partial or full removal of the embolic obstruction from the patient. In alternative embodiments the dimensional and material characteristics of the cell structures 26 in the main body portion 16 are selected to produce a radial force per unit length of between about 0.005 N/mm to about 0.050 N/mm, preferable between about 0.010 N/mm to about 0.050 N/mm, and more preferably between about 0.030 N/mm and about 0.050 N/mm. In one embodiment, the diameter of the main body portion 16 in a fully expanded state is about 4.0 millimeters with the cell pattern, strut dimensions and material being selected to produce a radial force of between about 0.040 N/mm to about 0.050 N/mm when the diameter of the main body portion is reduced to 1.5 millimeters. In the same or alternative embodiment, the cell pattern, strut dimensions and material(s) are selected to produce a radial force of between about 0.010 N/mm to about 0.020 N/mm when the diameter of the main body portion is reduced to 3.0 millimeters.

In the embodiments of FIGS. 1A and 1B, each of the cell structures 26 are shown having the same dimensions with each cell structure including a pair of short struts 32 and a pair of long struts 34. In an exemplary embodiment, struts 32 have a length of between about 0.080 and about 0.100 inches, struts 34 have a length of between about 0.130 and about 0.140 inches, with each of struts 32 and 34 having an as-cut width and thickness of about 0.003 inches and about 0.0045 inches, respectively, and a post-polishing width and thickness of between about 0.0022 inches and about 0.0039 inches, respectively. An advantage of having a strut thickness to width ratio of greater than one is that it promotes integration of the strut into the embolic obstruction. In alternative embodiments, the post-polishing width and thickness dimensions varies between about 0.0020 inches to about 0.0035 and about 0.0030 inches to about 0.0040 inches, respectively, with the thickness to width ratio varying between about 1.0 to about 2.0, and preferably between about 1.25 to about 1.75.

In one embodiment, only the strut elements of the main body portion 16 have a thickness to width dimension ratio of greater than one. In another embodiment, only the strut elements of the main body portion 16 and distal end portion 18 have a thickness to width dimension ratio of greater than one. In another embodiment, only a portion of the strut elements have a thickness to width dimension ratio of greater than one. In yet another embodiment, strut elements in different parts of the expandable member have different thickness to width dimension ratios, the ratios in each of the parts being greater than one. As an example, because the radial force exerted by the proximal end portion 14 and distal end portion 18 of the expandable member 12 may generally be less than the radial force exerted by the main body portion 16, the strut elements in the distal and/or proximal end portions can have a thickness to width ratio that is greater than the thickness to width ratio of the struts in the main body portion 16. An advantage of this construction is that the ability of the expandable member 12 to integrate into an embolic obstruction is made to be more uniform along the length of the expandable member.

In other embodiments, certain, or all of the strut elements have a tapered shape with the outer face of the strut having a width dimension less than the width dimension of the inner face of the strut. In other embodiments, the expandable member 12 may comprise strut elements having a generally rectangular cross-section and also strut elements having a tapered shape.

It is important to note that the present invention is not limited to expandable members 12 having uniform cell structures nor to any particular dimensional characteristics. As an example, in alternative embodiments the cell structures 26 in the proximal and/or distal end portions 14 and 18 are either larger or smaller in size than the cell structures 26 in the main body portion 16. In one embodiment, the cell structures 26 in the proximal and distal end portions 14 and 18 are sized larger than those in the main body portion 16 so that the radial forces exerted in the end portions 14 and 18 are lower than the radial forces exerted in the main body portion 16.

The radial strength along the length of the expandable member 12 may be varied in a variety of ways. One method is to vary the mass (e.g., width and/or thickness) of the struts along the length of the expandable member 12. Another method is to vary the size of the cell structures 26 along the length of the expandable member 12. The use of smaller cell structures will generally provide higher radial forces than those that are larger. Varying the radial force exerted along the length of the expandable member can be particularly advantageous for use in entrapping and retrieving embolic obstructions. For example, in one embodiment the radial force in the distal section of the main body portion 16 of the expandable member 12 in its expanded state is made to be greater than the radial force in the proximal section of the main body portion 16. Such a configuration promotes a larger radial expansion of the distal section of the main body portion 16 into the embolic obstruction as compared to the proximal section. Because the expandable member 12 is pulled proximally during the removal of the embolic obstruction from the patient, the aforementioned configuration will reduce the likelihood of particles dislodging from the embolic obstruction during its removal. In an alternative embodiment the radial force in the proximal section of the main body portion 16 of the expandable member 12 in its expanded state is made to be greater than the radial force in the distal section of the main body portion 16. In yet another embodiment, the main body portion 16 of the expandable member 12 includes a proximal section, a midsection and a distal section with the radial force in the proximal and distal sections being larger than the radial force in the midsection when the expandable member 12 is in an expanded state.

Figure 9:
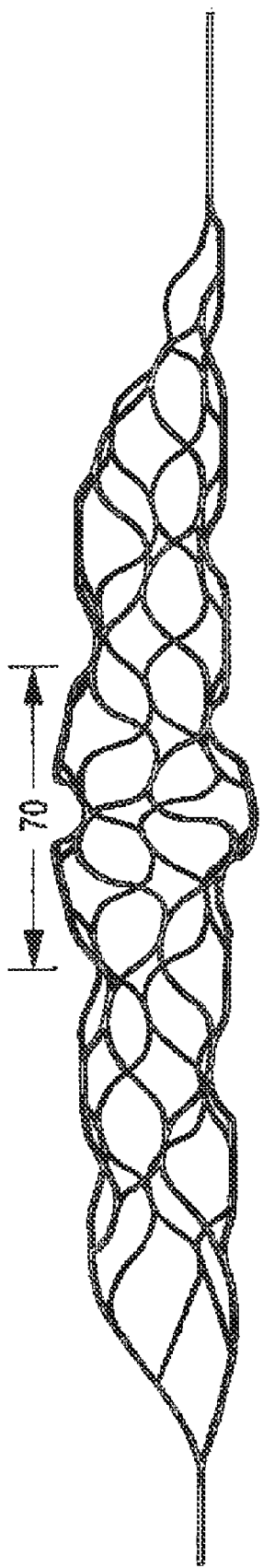
FIG. 9 illustrates an expandable member in an expanded position having a bulge or increased diameter portion.

In alternative embodiments, as exemplified in FIG. 9, the main body portion 16 may include an increased diameter portion or bulge 70 to enhance the expandable member's ability to entrap or otherwise engage with an embolic obstruction. In FIG. 9, a single increased diameter portion 70 is provided within the midsection of main body portion 16. In alternative embodiments, the increased diameter portion 70 may be positioned proximally or distally to the midsection. In yet other embodiments, two or more increased diameter portions 70 may be provided along the length of the main body portion 16. In one implementation, the two or more increased diameter portions 70 have essentially the same manufactured nominal diameter. In another implementation, the distal-most increased diameter portion 70 has a greater manufactured nominal diameter than the proximally disposed increased diameter portions. In alternative exemplary embodiments the nominal diameter of the increased diameter portion 70 is between about 25.0 to about 45.0 percent greater than the nominal diameter of the main body portion. For example, in one embodiment, the nominal expanded diameter of main body portion 16 is about 3.0 millimeters and the nominal diameter of the increased diameter portion 70 is about 4.0 millimeters. In another embodiment the nominal expanded diameter of main body portion 16 is about 3.50 millimeters and the nominal diameter of the increased diameter portion 70 is about 5.00 millimeters. In one embodiment, the one or more increased diameter portions 70 are formed by placing an expandable mandrel into the internal lumen of the main body portion 16 and expanding the mandrel to create the increased diameter portion 70 of a desired diameter. In another embodiment, one or more of the increased diameter portions 70 are formed by placing a mandrel of a given width and diameter into the main body portion 16 and then crimping the expandable member 12 in a manner to cause at least a portion of the main body portion 16 to be urged against the mandrel.

In one embodiment, the strut elements in the increased diameter portion or portions 70 have a thickness dimension to width dimension ratio that is greater than the thickness to width ratio of the other struts in the main body portion 16. In yet another embodiment, the strut elements in the increased diameter portion or portions 70 have a thickness dimension to width dimension ratio that is less than the thickness to width ratio of the other struts in the main body portion 16.

Figure 2:
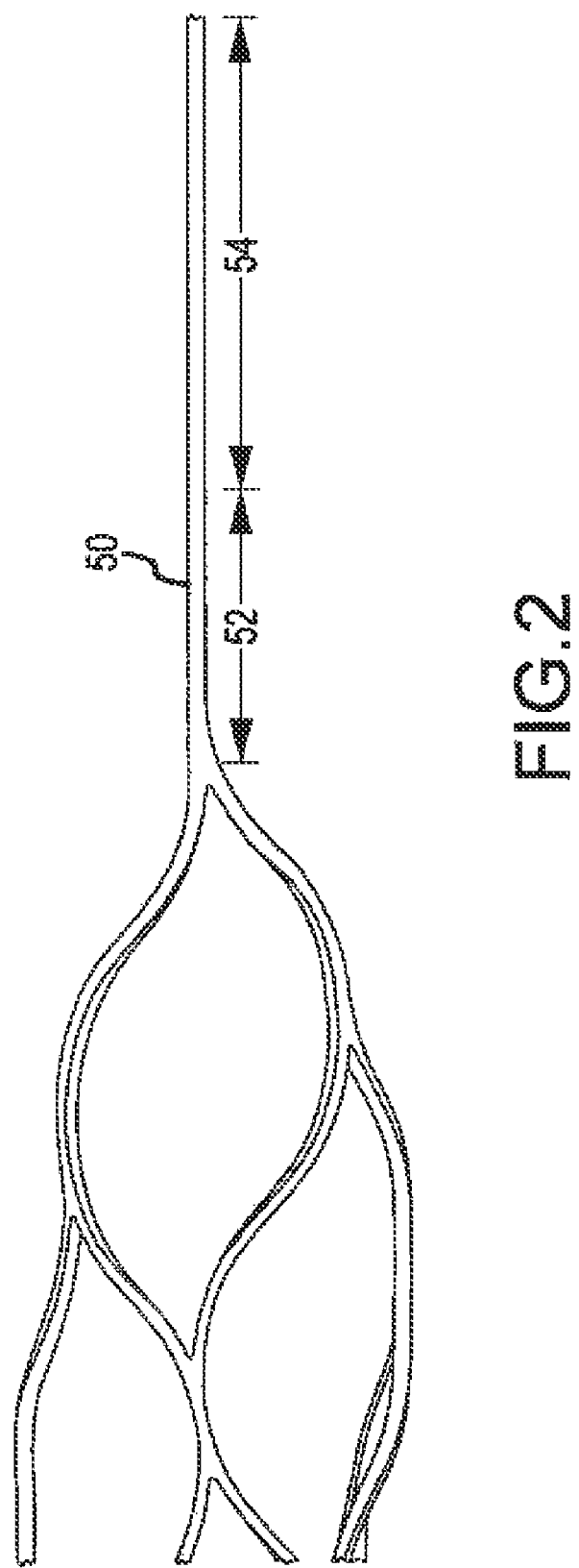
FIG. 2 illustrates a distal wire segment that extends distally from an expandable member in one embodiment.

In one implementation, a distal wire segment 50, that is attached to or integrally formed with expandable member 12, extends distally from the distal end 22 of the expandable member 12 and is configured to assist in guiding the delivery of the expandable member to the treatment site of a patient. FIG. 2 shows a distal wire segment 50 in one embodiment having a first section 52 of a uniform cross-section and a second section 54 having a distally tapering cross-section. In an exemplary embodiment, the first section 52 has a length of about 3.0 millimeters and an as-cut cross-sectional dimension of about 0.0045 inches by about 0.003 inches, and whereas the second section 54 has a length of about 4.0 millimeters and tapers to a distal-most, as-cut, cross-sectional dimension of about 0.002 inches by about 0.003 inches. Post-polishing of the device generally involves an etching process that typically results in a 40% to 50% reduction in the as-cut cross-sectional dimensions. In another embodiment, as depicted in FIG. 3, the distal wire segment 50 is bound by a spring member 57 of a uniform diameter and is equipped with an atruamatic distal tip 58. In alternative embodiments, the spring element 57 and/or the atraumatic tip 58 are made or coated with of a radiopaque material, such as, for example, platinum.

Figure 28B:
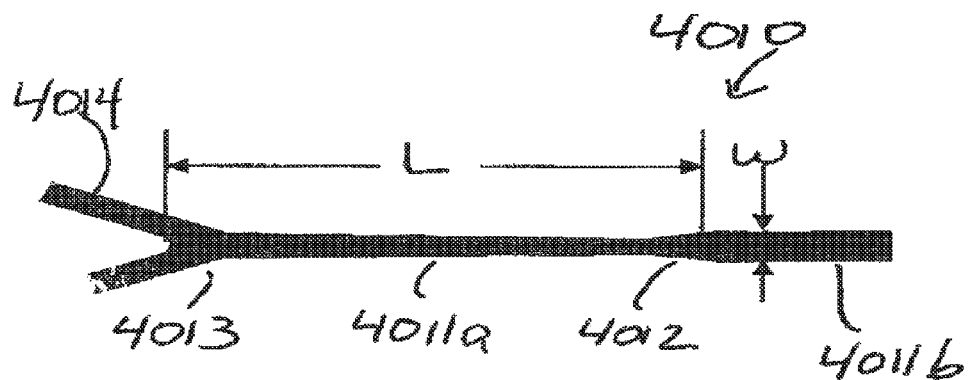

FIG. 28b illustrates an alternative distal wire segment construction. As depicted, the distal wire segment 4010 includes a first section 4011a and a second section 4011b, the second section 4011b having a width W greater than the width of the first section 4011a. In one implementation a tapered transition section 4012 joins the first and second sections 4011a and 4011b. In one implementation the width W of the second section is between about 0.003 inches and about 0.004 inches with the length L between the distal end 4013 of the expandable member 4014 and the second section 4011b of the wire segment 4010 being between about 0.015 inches and about 0.020 inches. An advantage of the inclusion of the second section 4011b is that the greater width dimension provides a larger surface area for bonding a coil/spring segment 57 to the wire segment 4010. In one implementation the first section 4011a has a circular or substantially circular construction and the second section 4011b has a flat profile formed by a pressing/coining operation.

In one embodiment, as will be described in more detail below, the expandable member 12 is delivered to the treatment site of a patient through the lumen of a delivery catheter that has been previously placed at the treatment site. In an alternative embodiment, the vascular treatment device 10 includes a sheath that restrains the expandable member 12 in a compressed state during delivery to the treatment site and which is proximally retractable to cause the expandable member 12 to assume an expanded state.

In one implementation, the expandable member 12 in the expanded state is able to engage an embolic obstruction residing at the treatment site, for example by embedding itself into the obstruction, and is removable from the patient by pulling on a portion of the elongate flexible wire 40 residing outside the patient until the expandable member 12 and at least a portion of the embolic obstruction are removed from the patient.

The use of interconnected and out-of-phase undulating elements 24 to create at least some of the cell structures 26 in alternative embodiments provides several advantages. First, the curvilinear nature of the cell structures 26 enhances the flexibility of the expandable member 12 during its delivery through the tortuous anatomy of the patient to the treatment site. In addition, the out-of-phase relationship between the undulating elements facilitates a more compact nesting of the expandable member elements permitting the expandable member 12 to achieve a very small compressed diameter. A particular advantage of the expandable member strut pattern shown in FIG. 1A, and various other embodiments described herein, is that they enable sequential nesting of the expandable member elements which permit the expandable members to be partially or fully deployed and subsequently withdrawn into the lumen of a delivery catheter. The out-of-phase relationship also results in a diagonal orientation of the cell structures 26 which may induce a twisting action as the expandable member 12 transitions between the compressed state and the expanded state that helps the expandable member to better engage with the embolic obstruction. In alternative embodiments, the cell structures 26 of the expandable member 12 are specifically arranged to produce a desired twisting action during expansion of the expandable member 12. In this manner, different expandable members each having different degrees of twisting action may be made available to treat, for example, different types of embolic obstructions.

To enhance visibility of the device under fluoroscopy, the expandable member may be fully or partially coated with a radiopaque material, such as tungsten, platinum, platinum/iridium, tantalum and gold. Alternatively, or in conjunction with the use of a radiopaque coating, radiopaque markers 60 may be positioned at or near the proximal and distal ends 20 and 22 of the expandable device and/or along the proximal and distal wire segments 42 and 50 and/or on selected expandable member strut segments. In one embodiment, the radiopaque markers 60 are radiopaque coils, such as platinum coils.

Figure 4A:
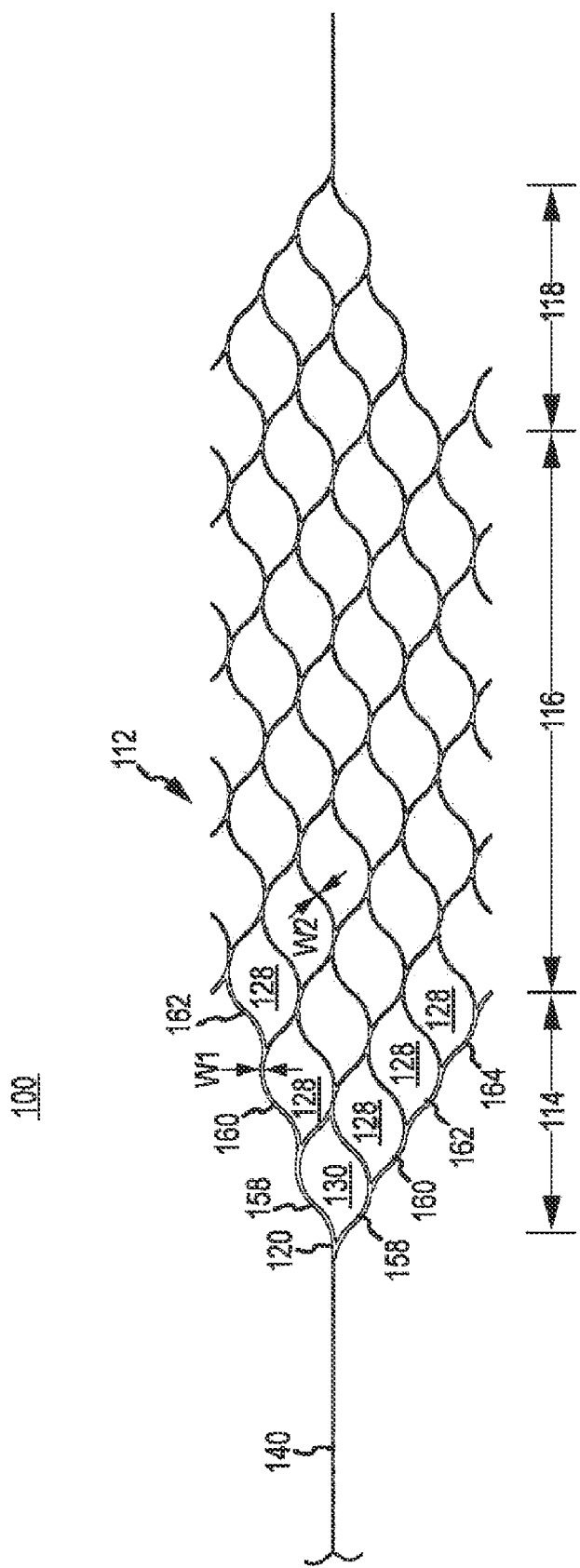
FIG. 4A illustrates a two-dimensional plane view of an expandable member of a treatment device in another embodiment.
Figure 4B:
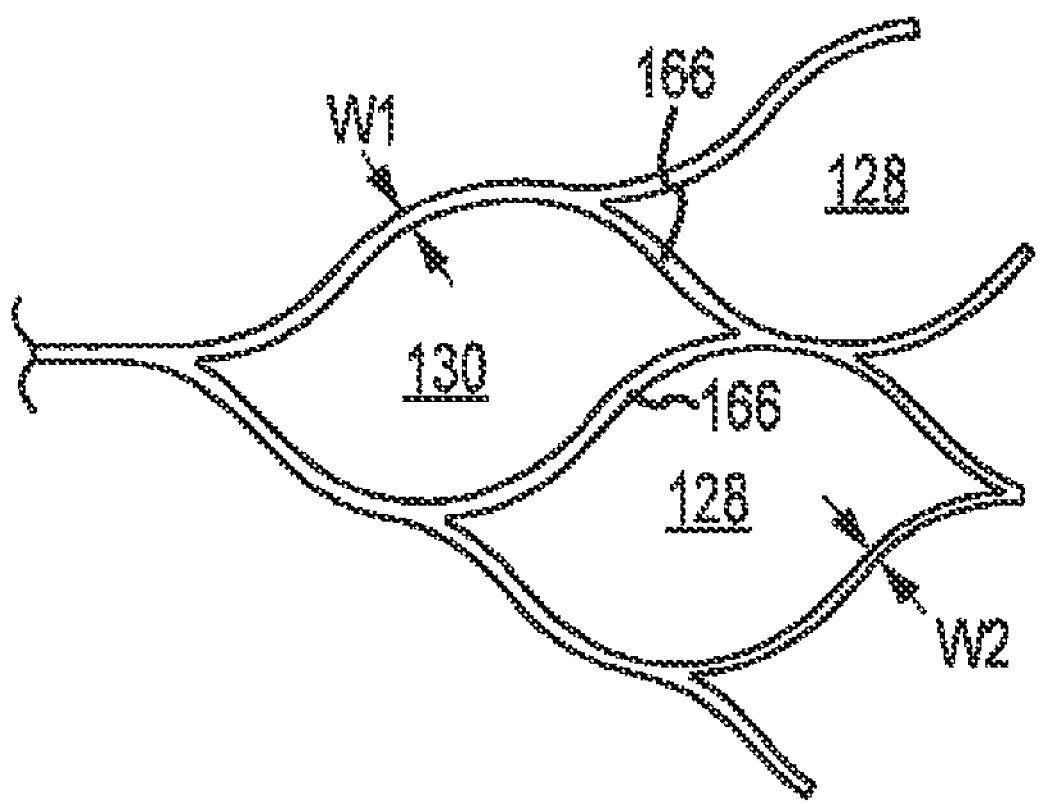
FIG. 4B is an enlarged view of the proximal-most segment of the expandable member illustrated in FIG. 4A.

FIG. 4A depicts a vascular treatment device 100 in a two-dimensional plane view in another embodiment of the present invention. In its manufactured and/or expanded tubular configuration, device 100 has a similar construction as device 10 shown in FIG. 1B. Like device 10 described above in conjunction with FIGS. 1A and 1B, device 100 includes a self-expandable member 112 that is coupled to an elongate flexible wire 140. The expandable member 112 includes a proximal end portion 114, a cylindrical main body portion 116 and a distal end portion 118. As mentioned above, delivery of the expandable member 112 in its unexpanded state to the treatment site of a patient is accomplished in one manner by placing the expandable member 112 into the proximal end of a delivery catheter and pushing the expandable member 112 through the lumen of the delivery catheter until it reaches a distal end of the catheter that has been previously placed at or across the treatment site. The proximally extending elongate flexible wire 140 which is attached to or coupled to the proximal end 120 of the expandable member 112 is designed to transmit a pushing force applied to it to its connection point with the elongate flexible member 112. As shown in FIG. 4A, and in more detail in FIG. 4B, device 100 is distinguishable from the various embodiments of device 10 described above in that the proximal-most cell structures 128 and 130 in the proximal end portion 114 include strut elements having a width dimension W1 larger than the width dimension W2 of the other strut elements within the expandable member 112. As shown, the proximal-most wall sections 160, 162 and 164 of cell structures 128 are made of struts having width W1. Moreover, all the struts of the proximal-most cell structure 130 have an enhanced width W1. The inclusion and placement of the struts with width W1 provides several advantages. One advantage is that they permit the push force applied by the distal end of the elongate wire 140 to the proximal end 120 of elongate member 112 to be more evenly distributed about the circumference of the expandable member 112 as it is being advanced through the tortuous anatomy of a patient. The more evenly distributed push force minimizes the formation of localized high force components that would otherwise act on individual or multiple strut elements within the expandable member 112 to cause them to buckle. Also, by including the struts of width W1 in the peripheral regions of proximal end portion 114, they greatly inhibit the tendency of the proximal end portion 114 to buckle under the push force applied to it by elongate wire 140. In one exemplary embodiment the as-cut width dimension W1 is about 0.0045 inches and the as-cut width dimension W2 is about 0.003 inches. As discussed above, post-polishing of the device generally involves an etching process that typically results in a 40% to 50% reduction in the as-cut cross-sectional dimensions.

It is important to note that although the width dimension W1 is shown as being the same among all struts having an enhanced width, this is not required. For example, in one embodiment wall segments 158 may have an enhanced width dimension greater than the enhanced width dimension of wall segments 160, and wall segments 160 may have an enhanced width dimension greater than the enhanced width dimension of wall segments 162, and so on. Moreover, the inner strut elements 166 of the proximal-most cell structure 130 may have an enhanced width dimension less than the enhanced width dimensions of struts 158. Also, in alternative embodiments, the radial thickness dimension of struts 158, 160, 162, 164, etc. may be enhanced in lieu of the width dimension or in combination thereof.

In yet another embodiment, as shown in FIG. 5, some of the strut elements 180 in the distal end portion 118 of the expandable member 112 have a mass greater than that of the other struts to resist buckling and possible breaking of the struts as device 100 is advanced to a treatment site of a patient. In the embodiment shown, struts 180 are dimensioned to have the same width as distal wire segment 150. In alternative embodiments, the thickness dimension of struts 180 may be enhanced in lieu of the width dimension or in combination thereof.

Figure 6B:
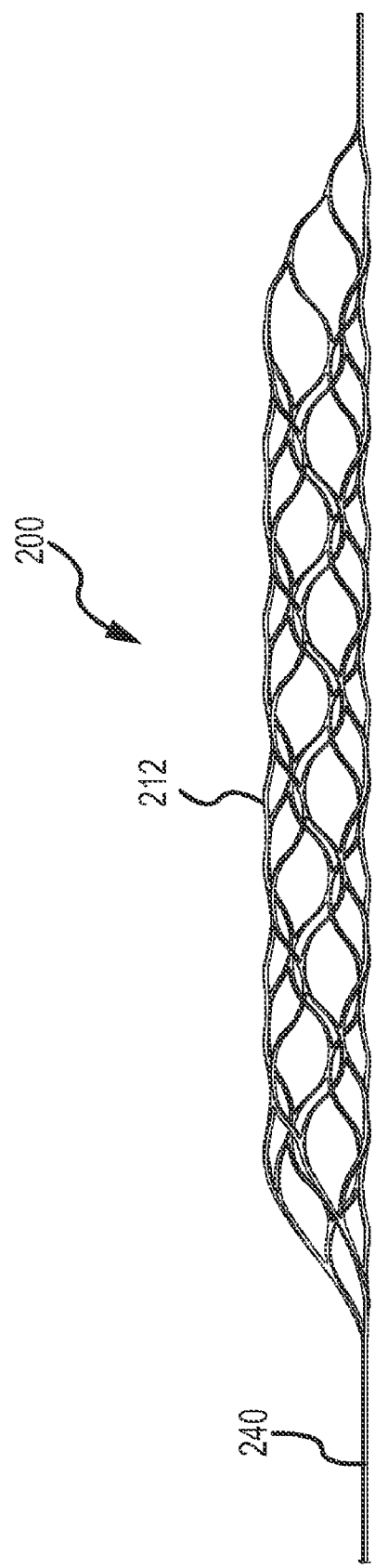
FIG. 6B is an isometric view of the expandable member illustrated in FIG. 6A.

FIGS. 6A and 6B illustrate a vascular treatment device 200 in accordance with another embodiment of the present invention. FIG. 6A depicts device 200 in a two-dimensional plane view as if the device were cut and laid flat on a surface. FIG. 6B depicts the device in its manufactured and/or expanded tubular configuration. Device 200 includes an expandable member 212 having a proximal end portion 214, a cylindrical main body portion 216 and a distal end portion 218 with an elongate flexible wire 240 attached to or otherwise coupled to the proximal end 220 of the expandable member. The construction of device 200 is similar to device 100 described above in conjunction with FIG. 4A except that the proximal wall segments 260 of cell structures 228 and 230 comprise linear or substantially linear strut elements as viewed in the two dimension plane view of FIG. 6A. In one embodiment, the linear strut elements 260 are aligned to form continuous and substantially linear rail segments 270 that extend from the proximal end 220 of proximal end portion 214 to a proximal-most end of main body portion 216 (again, as viewed in the two dimension plane view of FIG. 6A) and preferably are of the same length, but may be of different lengths. When the pattern of FIG. 6A is applied to laser cutting a tubular structure, the resulting expandable member configuration is that as shown in FIG. 6B. As shown in FIG. 6B, rail segments 270 are not in fact linear but are of a curved and non-undulating shape. This configuration advantageously provides rail segments 270 devoid of undulations thereby enhancing the rail segments' ability to distribute forces and resist buckling when a push force is applied to them. In alternative preferred embodiments, the angle θ between the wire segment 240 and rail segments 270 ranges between about 140 degrees to about 150 degrees. In one embodiment, one or both of the linear rail segments 270 have a width dimension W1 which is greater than the width dimension of the adjacent strut segments of cell structures 228 and 230. An enhanced width dimension W1 of one or both the linear rail segments 270 further enhances the rail segments' ability to distribute forces and resist buckling when a push force is applied to them. In another implementation, one or both of the linear rail segments 270 are provided with an enhanced thickness dimension, rather than an enhanced width dimension to achieve the same or similar result. In yet an alternative implementation, both the width and thickness dimensions of one or both of the linear rail segments 270 are enhanced to achieve the same or similar results. In yet another implementation, the width and/or thickness dimensions of each of the rail segments 270 differ in a manner that causes a more even compression of the proximal end portion 214 of the expandable member 212 when it is loaded or retrieved into a delivery catheter or sheath (not shown).

Figure 7B:
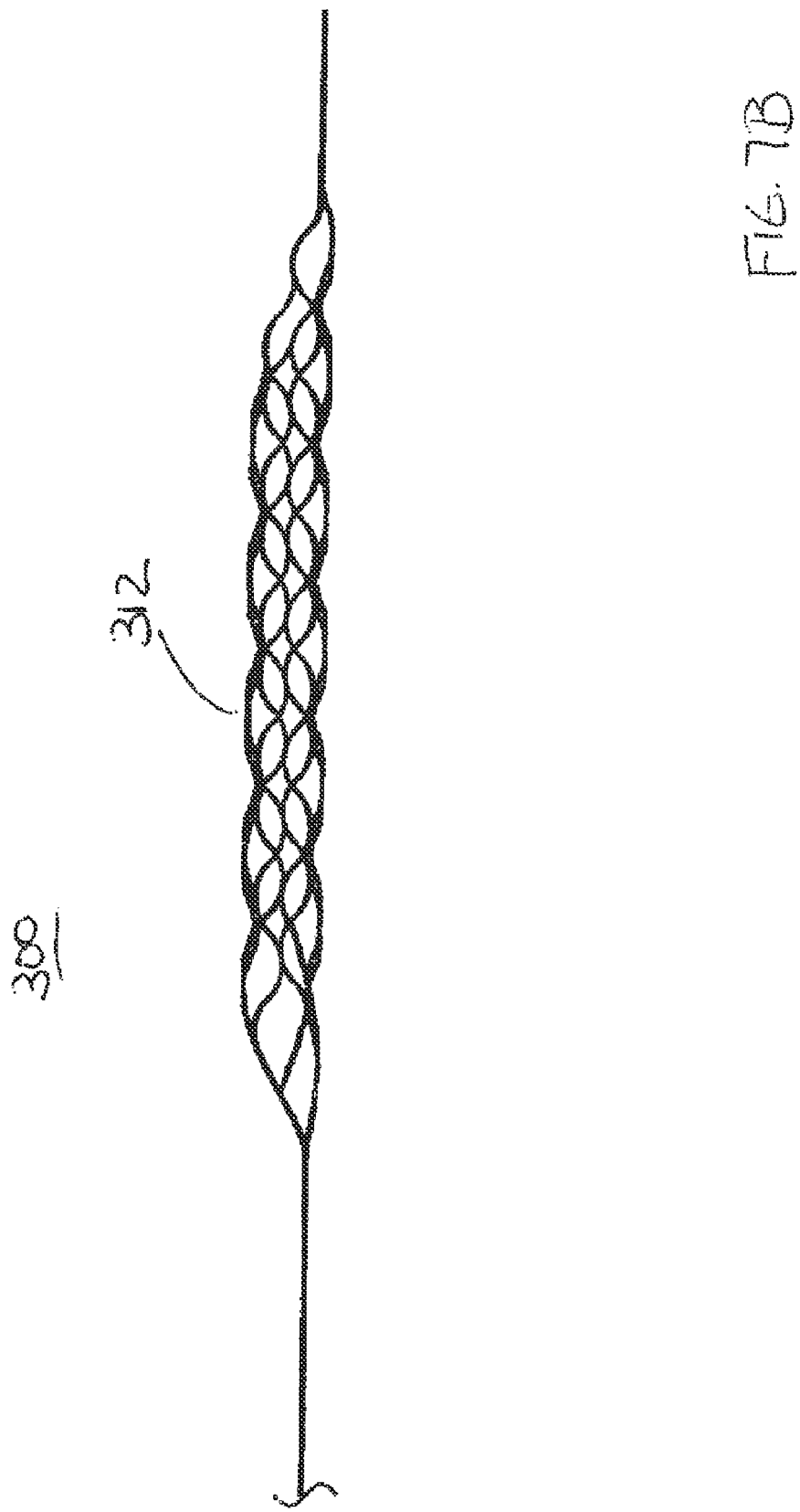
FIG. 7B is an isometric view of the expandable member illustrated in FIG. 7A.

FIGS. 7A and 7B illustrate a vascular treatment device 300 in accordance with another embodiment of the present invention. FIG. 7A depicts device 300 in a two-dimensional plane view as if the device were cut and laid flat on a surface. FIG. 7B depicts the device in its manufactured and/or expanded tubular configuration. Device 300 includes an expandable member 312 having a proximal end portion 314, a cylindrical main body portion 316 and a distal end portion 318 with an elongate flexible wire 340 attached to or otherwise coupled to the proximal end 320 of the expandable member. The construction of device 300 is similar to device 200 described above in conjunction with FIGS. 6A and 6B except that the proximal-most cell structure 330 comprises a substantially diamond shape as viewed in the two-dimensional plane of FIG. 7A. The substantially diamond-shaped cell structure includes a pair of outer strut elements 358 and a pair of inner strut elements 360, each having an enhanced width and/or enhanced thickness dimension as previously discussed in conjunction with the embodiments of FIGS. 4 and 6. In alternative preferred embodiments, the inner strut elements 360 intersect the outer strut elements 358 at an angle β between about 25.0 degrees to about 45.0 degrees as viewed in the two-dimensional plane view of FIG. 7A. Maintaining the angular orientation between the inner and outer struts within in this range enhances the pushabilty of the expandable member 312 without the occurrence of buckling and without substantially affecting the expandable member's ability to assume a very small compressed diameter during delivery.

Figure 7C:
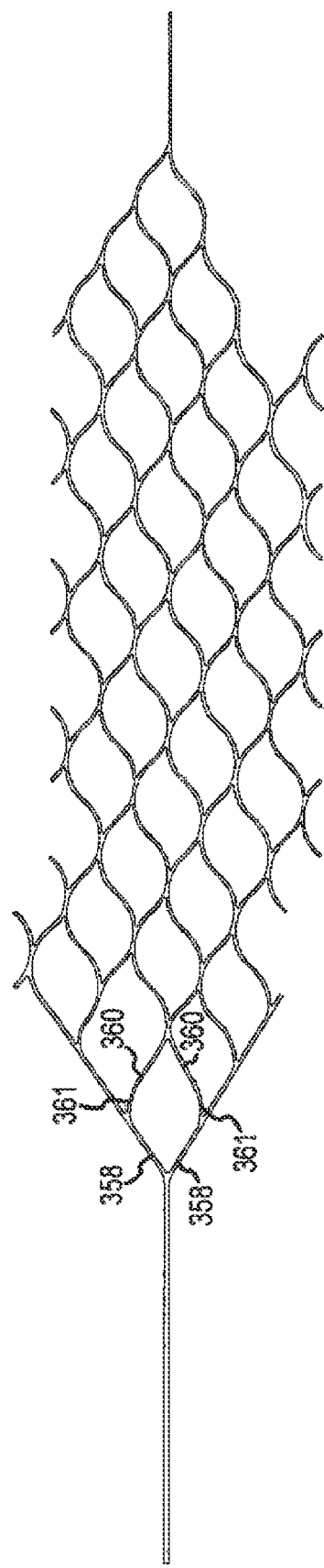
FIG. 7C illustrates a two-dimensional plane view of an expandable member of a treatment device in another embodiment.

In one embodiment, the inner strut elements 360 have a mass less than that of the outer strut elements 358 that enables them to more easily bend as the expandable member 312 transitions from an expanded state to a compressed state. This assists in achieving a very small compressed diameter. In another embodiment, as shown in FIG. 7C, the inner strut elements 360 are coupled to the outer strut elements 358 by curved elements 361 that enable the inner strut elements 360 to more easily flex when the expandable member 312 is compressed to its delivery position.

Figure 8:
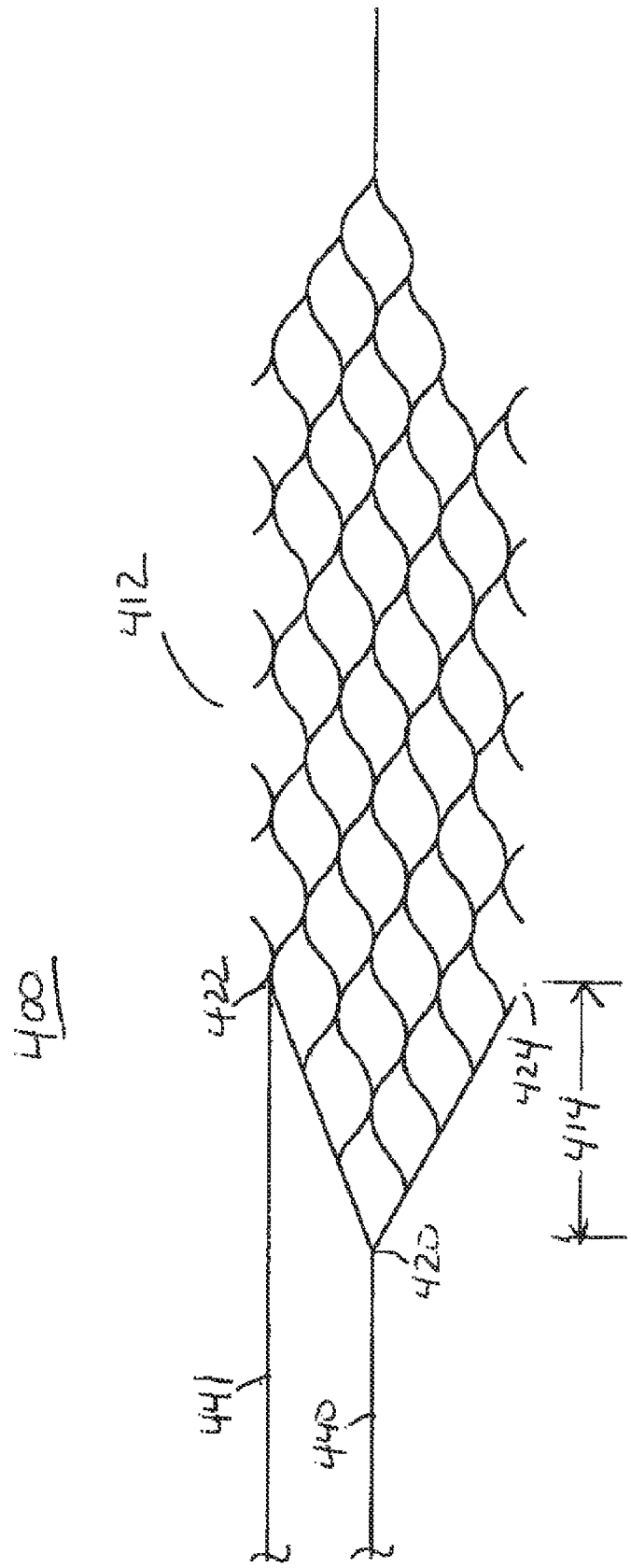
FIG. 8 illustrates a two-dimensional plane view of an expandable member of a treatment device in another embodiment.

FIG. 8 illustrates an alternative embodiment of a vascular treatment device 400. Device 400 has a similar construction to that of device 200 depicted in FIGS. 6A and 6B with the exception that the expandable member 412 of device 400 is connected at its proximal end portion 414 with two distally extending elongate flexible wires 440 and 441. As illustrated, wire 440 is attached to or otherwise coupled to the proximal-most end 420 of proximal end portion 414, while wire 441 is attached to or otherwise coupled to the distal-most end 422 of the proximal end portion 414 at the junction with rail segment 470. In yet another embodiment, an additional elongate flexible wire (not shown) may be attached to the distal-most end 424. The use of two or more elongate flexible wires 440 and 441 to provide pushing forces to the proximal end portion 414 of elongate member 412 advantageously distributes the pushing force applied to the proximal end portion 414 to more than one attachment point.

FIG. 10 illustrates a two-dimensional plane view of a vascular treatment device 500 in another embodiment of the present invention. In the embodiment of FIG. 10, expandable member 512 includes a plurality of generally longitudinal undulating elements 524 with adjacent undulating elements being out-of-phase with one another and connected in a manner to form a plurality of diagonally disposed cell structures 526. The expandable member 512 includes a cylindrical portion 516 and a distal end portion 518 with the cell structures 526 in the main body portion 516 extending continuously and circumferentially around a longitudinal axis 530 of the expandable member 512. The cell structures 526 in the distal end portion 518 extend less than circumferentially around the longitudinal axis 530 of the expandable member 512. Attached to or otherwise coupled to each of the proximal-most cell structures 528 are proximally extending elongate flexible wires 540. The use of multiple elongate flexible wires 540 enables the pushing force applied to the proximal end of the expandable member 512 to be more evenly distributed about its proximal circumference. In another embodiment, although not shown in FIG. 10, the proximal-most strut elements 528 have a width and/or thickness greater than the struts in the other portions of the expandable member 512. Such a feature further contributes to the push force being evenly distributed about the circumference of the expandable member 512 and also inhibits the strut elements directly receiving the push force from buckling.

Figure 11A:
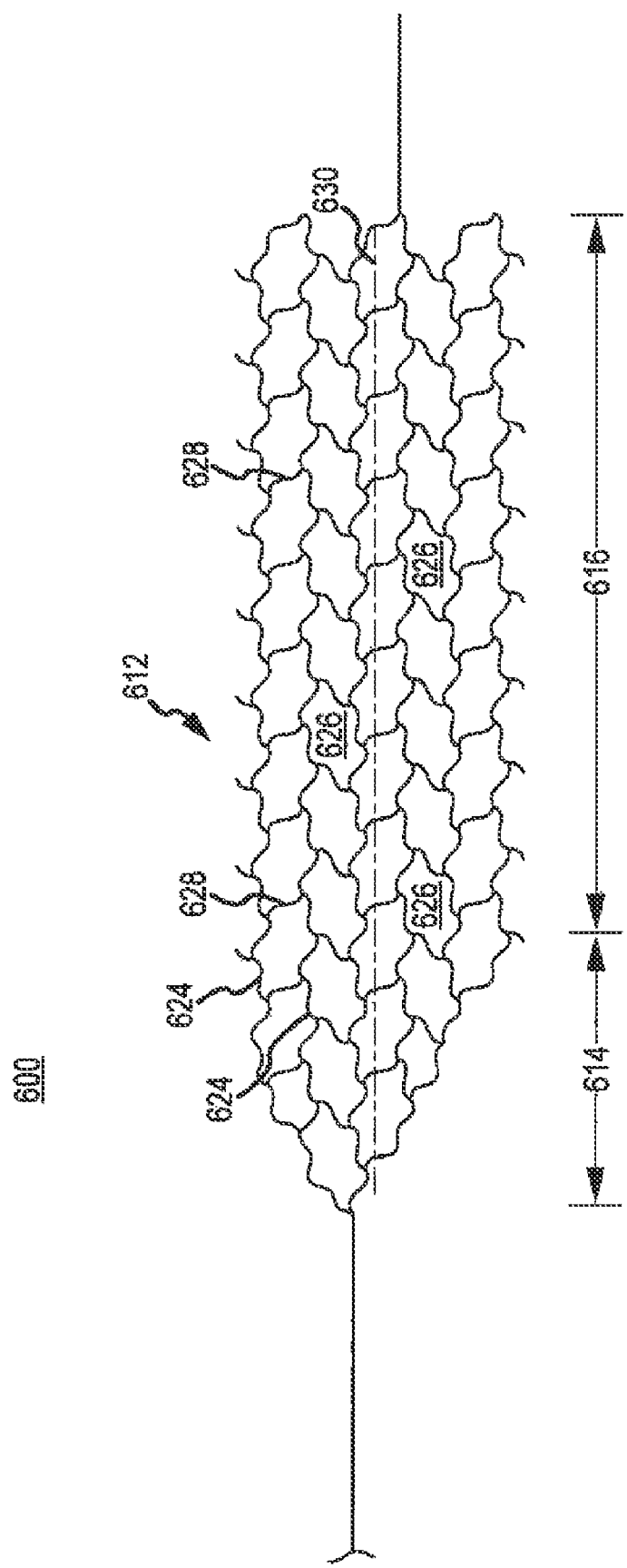
FIG. 11A illustrates a two-dimensional plane view of an expandable member of a treatment device in one implementation.

FIGS. 11A and 11B illustrate a vascular treatment device 600 in accordance with another embodiment of the present invention. FIG. 11A depicts device 600 in a two-dimensional plane view as if the device were cut and laid flat on a surface. FIG. 11B depicts the device in its manufactured and/or expanded tubular configuration. In the embodiment of FIGS. 11A and 11B, expandable member 612 includes a plurality of generally longitudinal undulating elements 624 with adjacent undulating elements being interconnected by a plurality of curved connectors 628 to form a plurality of closed-cell structures 626 disposed about the length of the expandable member 612. In the embodiment shown, the expandable member 612 includes a proximal end portion 614 and a cylindrical portion 616 with the cell structures 626 in the cylindrical portion 616 extending continuously and circumferentially around a longitudinal axis 630 of the expandable member 612. The cell structures 626 in the proximal end portion 614 extend less than circumferentially around the longitudinal axis 630 of the expandable member 612. In an alternative embodiment, the expandable member 612 includes a proximal end portion, a cylindrical main body portion and a distal end portion, much like the expandable member 12 depicted in FIGS. 1A and 1B. In such an embodiment, the cell structures 626 in the distal end portion of the expandable member would extend less than circumferentially around the longitudinal axis 630 of the expandable member 612 in a manner similar to the proximal end portion 614 shown in FIG. 11A. Moreover, it is appreciated that the expandable members of FIGS. 1A, 4A, 6A, 7A, 7C, 10, 14, 15 and 19-24 may be modified in a way so as to eliminate the distal end portion (e.g., distal end portion 18 in FIG. 1A) so that there exists only a proximal end portion and main body portion like that of FIG. 11A.

Figure 12:
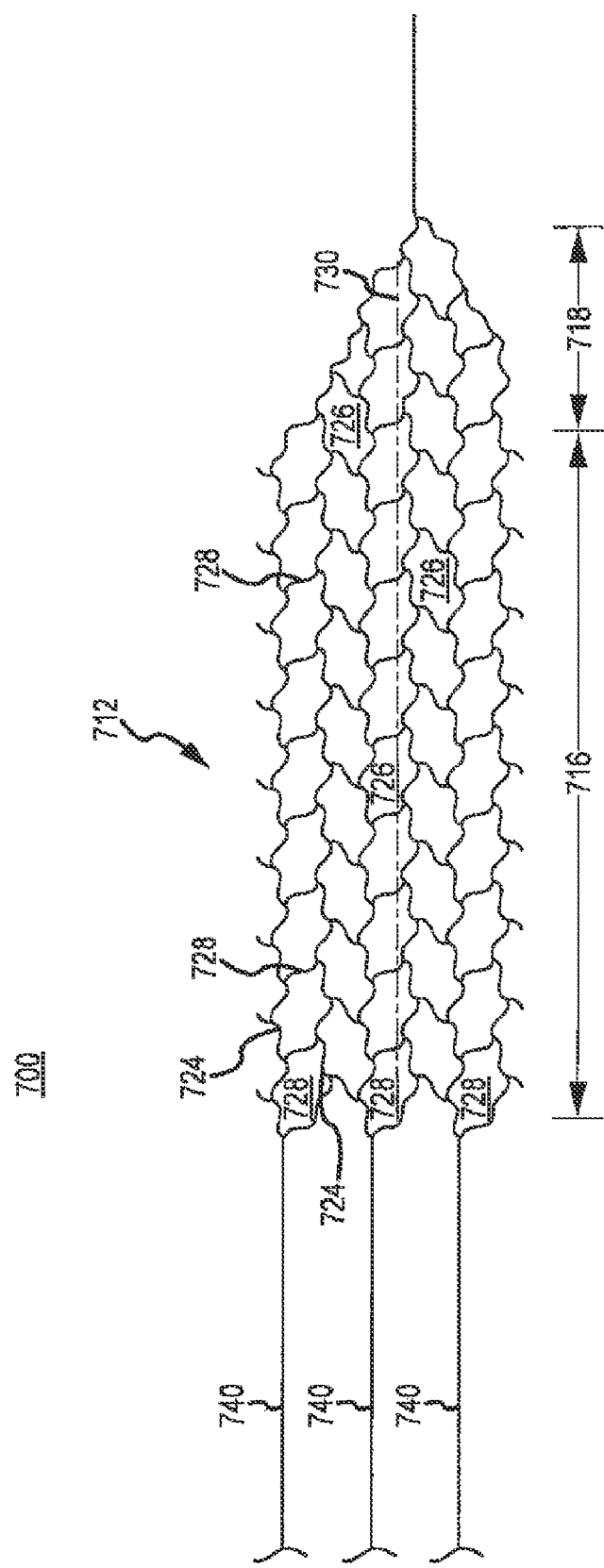
FIG. 12 illustrates a two-dimensional plane view of an expandable member of a treatment device in another implementation.

FIG. 12 illustrates a vascular treatment device 700 in accordance with another embodiment of the present invention. FIG. 12 depicts device 700 in a two-dimensional plane view as if the device were cut and laid flat on a surface. In the embodiment of FIG. 12, expandable member 712 includes a plurality of generally longitudinal undulating elements 724 with adjacent undulating elements being interconnected by a plurality of curved connectors 728 to form a plurality of closed-cell structures 726 disposed about the length of the expandable member 712. In the embodiment shown, the expandable member 712 includes a cylindrical portion 716 and a distal end portion 718 with the cell structures 726 in the cylindrical portion 716 extending continuously and circumferentially around a longitudinal axis 730 of the expandable member 712. The cell structures 726 in the distal end portion 718 extend less than circumferentially around the longitudinal axis 730 of the expandable member 712. In a manner similar to that described in conjunction with the embodiment of FIG. 10, attached to or otherwise coupled to each of the proximal-most cell structures 728 are proximally extending elongate flexible wires 740. This arrangement enables the pushing force applied to the proximal end of the expandable member 712 to be more evenly distributed about its proximal circumference. In another embodiment, although not shown in FIG. 12, the proximal-most strut elements 730 have a width and/or thickness greater than the struts in the other portions of the expandable member 712. Such a feature further contributes to the push force being evenly distributed about the circumference of the expandable member 712 and also inhibits the strut elements directly receiving the push force from buckling.

Figure 13C:
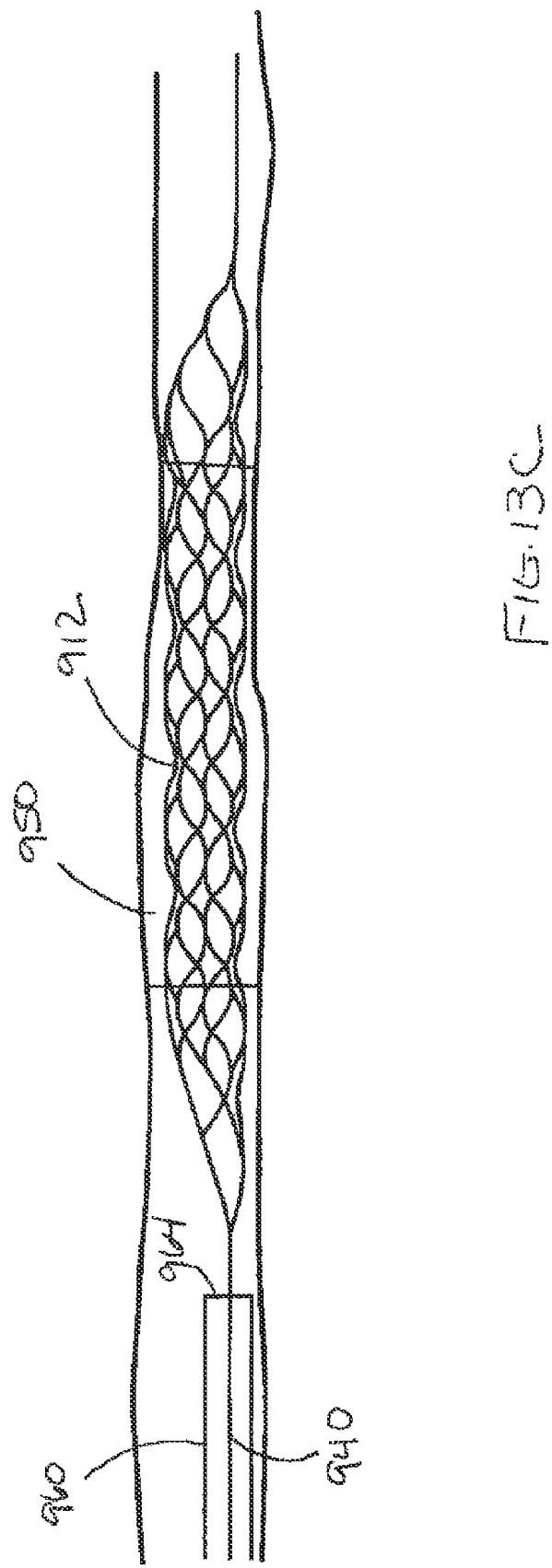

As previously discussed, in use, the expandable members of the present invention are advanced through the tortuous vascular anatomy of a patient to a treatment site, such as an embolic obstruction, in an unexpanded or compressed state of a first nominal diameter and are movable from the unexpanded state to a radially expanded state of a second nominal diameter greater than the first nominal diameter for deployment at the treatment site. One manner of delivering and deploying expandable member 912 at the site of an embolic obstruction 950 is shown in FIGS. 13A through 13C. As shown in FIG. 13A, a delivery catheter 960 having an inner lumen 962 is advanced to the site of the embolic obstruction 950 so that its distal end 964 is positioned distal to the obstruction. After the delivery catheter 960 is in position at the embolic obstruction 950, the retrieval device 900 is placed into the delivery catheter by introducing the expandable member 912 into a proximal end of the delivery catheter (not shown) and then advancing the expandable member 912 through the lumen 962 of the delivery catheter by applying a pushing force to elongate flexible wire 940. By the use of radiopaque markings and/or coatings positioned on the delivery catheter 960 and device 900, the expandable member 912 is positioned at the distal end of the delivery catheter 960 as shown in FIG. 13B so that the main body portion 916 is longitudinally aligned with the obstruction 950. Deployment of the expandable member 912 is achieved by proximally withdrawing the delivery catheter 960 while holding the expandable member 912 in a fixed position as shown in FIG. 13C. Once the expandable member 912 has been deployed to an expanded position within the obstruction 950, the expandable member 912 is retracted, along with the delivery catheter 960, to a position outside the patient. In one embodiment, the expandable member 912 is first partially retracted to engage with the distal end 964 of the delivery catheter 960 prior to fully retracting the devices from the patient.

In one embodiment, once the expandable member 912 is expanded at the obstruction 950, it is left to dwell there for a period of time in order to create a perfusion channel through the obstruction that causes the obstruction to be lysed by the resultant blood flow passing through the obstruction. In such an embodiment, it is not necessary that the expandable member 912 capture a portion of the obstruction 950 for retrieval outside the patient. When a sufficient portion of the obstruction 950 has been lysed to create a desired flow channel through the obstruction, or outright removal of the obstruction is achieved by the resultant blood flow, the expandable member 912 may be withdrawn into the delivery catheter 960 and subsequently removed from the patient.

In another embodiment, the expandable member 912 is expanded at the obstruction 950 and left to dwell there for a period of time in order to create a perfusion channel through the obstruction that causes the obstruction to be acted on by the resultant flow in a manner that makes the embolic obstruction more easily capturable by the expandable member and/or to make it more easily removable from the vessel wall of the patient. For example, the blood flow created through the embolic obstruction may be made to flow through the obstruction for a period of time sufficient to change the morphology of the obstruction that makes it more easily captured by the expandable member and/or makes it more easily detachable from the vessel wall. As in the preceding method, the creation of blood flow across the obstruction 950 also acts to preserve tissue. In one embodiment, the blood flow through the obstruction may be used to lyse the obstruction. However, in this modified method, lysing of the obstruction is performed for the purpose of preparing the obstruction to be more easily captured by the expandable member 912. When the obstruction 950 has been properly prepared, for example by creating an obstruction 950 of a desired nominal inner diameter, the expandable member 912 is deployed from the distal end 964 of the delivery catheter 940 to cause it to engage with the obstruction. Removal of all, or a portion, of the obstruction 950 from the patient is then carried out in a manner similar to that described above.

In yet another embodiment, once the expandable member 912 has been delivered and expanded inside the obstruction 950, it may be detached from the elongate wire 940 for permanent placement within the patient. In such an embodiment, the manner in which the elongate wire 940 is attached to the expandable member 912 allows the two components to be detached from one another. This may be achieved, for example, by the use of a mechanical interlock or an erodable electrolytic junction between the expandable member 912 and the elongate wire 940.

As described herein, the expandable members of the various embodiments may or may not include distal wire segments that are attached to their distal ends. In alternative preferred embodiments, vascular treatment devices that are configured to permanently place an expandable member at the site of an embolic obstruction do not include distal wire segments attached to the distal ends of the expandable members.

One advantage associated with the expandable member cell patterns of the present invention is that withdrawing the expandable members by the application of a pulling force on the proximal elongate wire flexible wire urges the expandable members to assume a smaller expanded diameter while being withdrawn from the patient, thus decreasing the likelihood of injury to the vessel wall. Also, during clot retrieval as the profile of the expandable members decrease, the cell structures collapse and pinch down on the clot to increase clot retrieval efficacy. Another advantage is that the cell patterns permit the expandable members to be retracted into the lumen of the delivery catheter after they have been partially or fully deployed. As such, if at any given time it is determined that the expandable member has been partially or fully deployed at an improper location, it may be retracted into the distal end of the delivery catheter and repositioned to the correct location.

Figure 14:
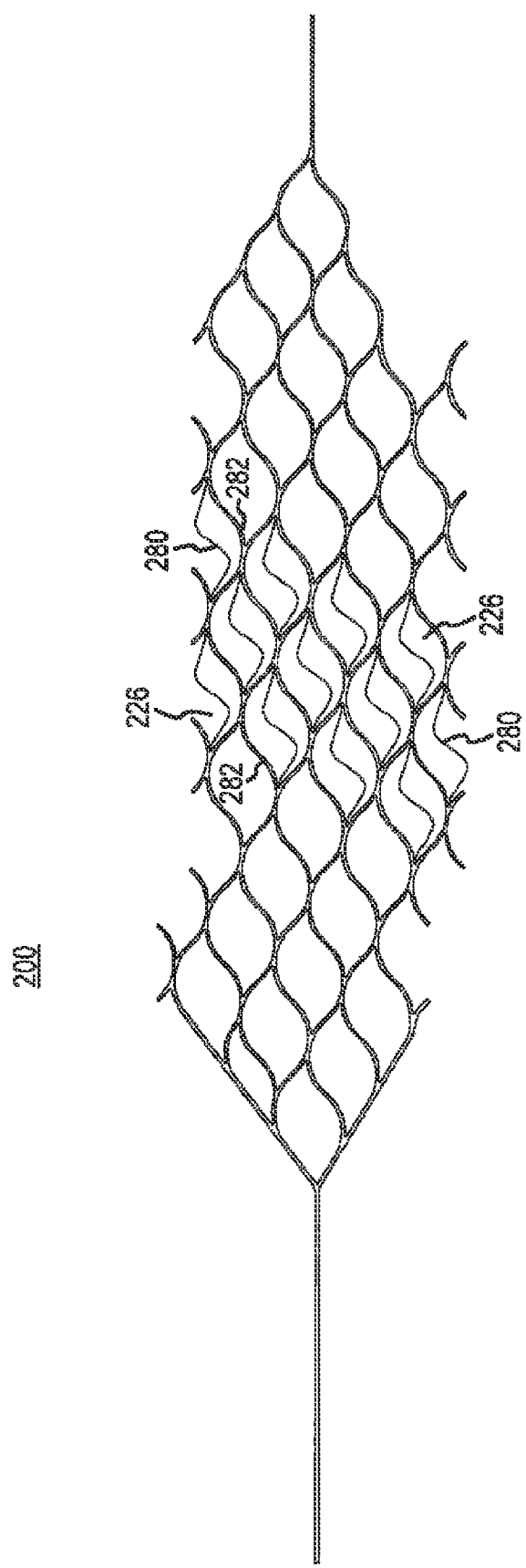
FIG. 14 illustrates a two-dimensional plane view of an expandable member of a treatment device in another embodiment.

With reference to FIG. 14, a modified version of the vascular treatment device 200 of FIG. 6A is shown that includes thin strut elements 280 intersecting at least some of the cell structures 226 located in the cylindrical main body portion 216 of expandable member 212. The thin strut elements 280 are dimensioned to have a width of less than the strut elements 282 that form the cell structures 226. In alternative exemplary embodiments, strut elements 280 have an as-cut or polished width dimension that is between about 25% to about 50% smaller than the respective as-cut or polished width dimension of struts 262. When used for the purpose of clot retrieval, a purpose of the thin struts 280 is to enhance the expandable member's ability to engage with and capture an embolic obstruction. This is accomplished by virtue of several factors.

Figure 15:
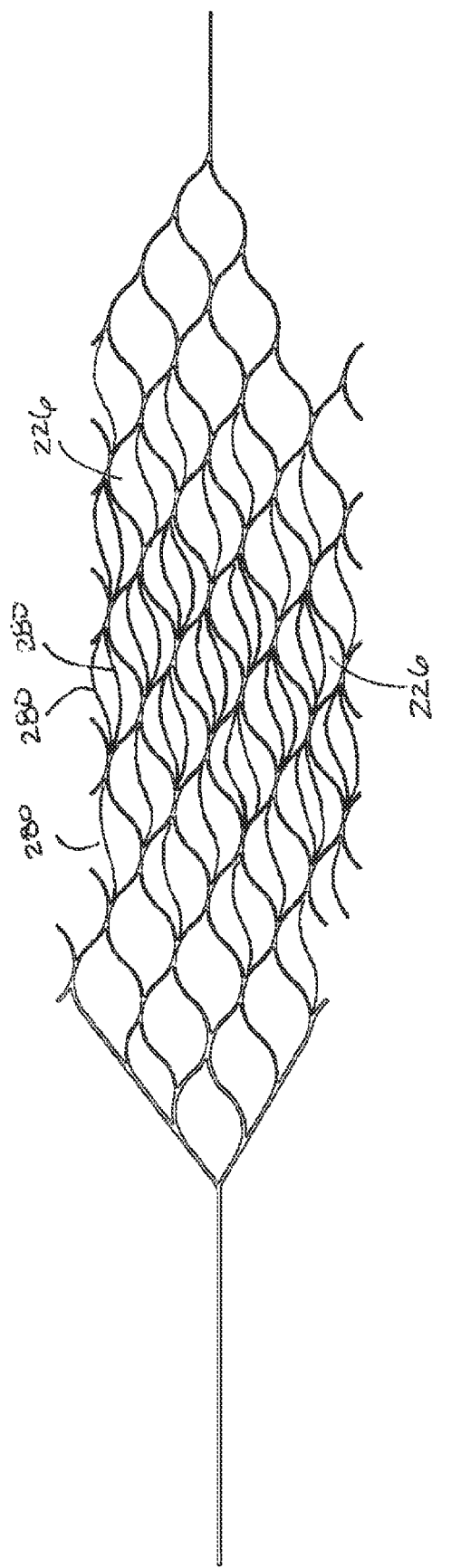
FIG. 15 illustrates a two-dimensional plane view of an expandable member of a treatment device in yet another embodiment.

First, the thinner width dimensions of the struts 280 make it easier for the struts to penetrate the obstruction. Second, they act to pinch portions of the entrapped obstruction against the outer and wider strut elements 282 as the expandable member is deployed within the obstruction. Third, they may be used to locally enhance radial forces acting on the obstruction. It is important to note that the use of thin strut elements 280 is not limited to use within cell structures 226 that reside within the cylindrical main body portion 216 of the expandable member 212. They may be strategically positioned in any or all of the cell structures of the expandable member. Moreover, it is important to note that the use of thin strut elements 280 is not limited to the embodiment of FIG. 6, but are applicable to all the various embodiments disclosed herein. Lastly, in alternative exemplary embodiments, as shown in FIG. 15, multiple thin strut elements 280 are provided within one or more of the cell structures 226, and may also be used in conjunction with cell structures that have a single thin strut element and/or cell structures altogether devoid of thin strut elements.

In the treatment of aneurysms when the treatment device is used for the purpose of diverting flow, the density of the cell structures 226 is sufficient to effectively divert flow away from the aneurysm sack. In alternative embodiments in lieu of, or in combination with adjusting the density of the cell structures 226, intermediate strut elements similar to the strut elements 280 of FIGS. 14 and 15 are used to increase the effective wall surface of the expandable member. In these embodiments, the intermediate strut elements may have the same, smaller, larger, or any combination thereof, dimensional characteristics of the cell structure struts. Conversely, in alternative embodiments for use in the treatment of aneurysms for the purpose placing coils or other like structures within the sack of the aneurysm, the size of the cell structures 226 is sufficient to facilitate passage of the coils through the cell structures.

Figure 16:
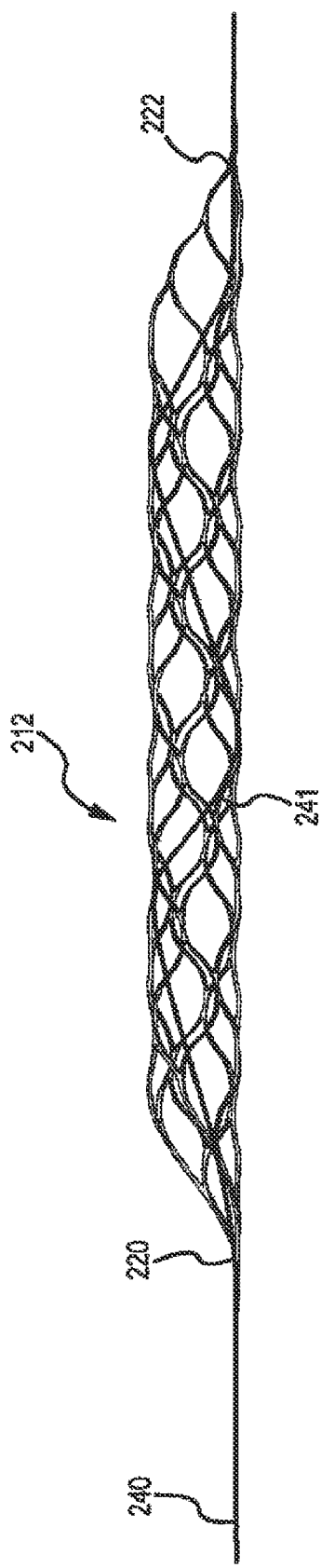
FIG. 16 illustrates an isometric view of an expandable member in another embodiment having an internal wire segment.

FIG. 16 illustrates a treatment device according to the embodiment of FIGS. 6A and 6B, wherein the pushability of the expandable member 212 during its advancement to the treatment site of a patient is enhanced by the inclusion of an internal wire segment 241 that extends between the proximal end 220 and distal end 222 of the expandable member 212. In this manner, the pushing force applied by elongate wire 240 is transmitted to both the proximal and distal ends of expandable device. The internal wire segment may be a discrete element that is attached to the proximal and distal ends of the expandable member, or may preferably be a co-extension of the elongate flexible wire 240. During delivery of the expandable member 212 to the treatment site in its compressed state, the internal wire segment 241 assumes a substantially straight or linear configuration so as to adequately distribute at least a part of the pushing force to the distal end 222 of the expandable member. When the expandable member 212 expands, it tends to foreshorten causing slack in the internal wire segment 241 that forms a long-pitched helix within the expandable member as shown in FIG. 16. An additional advantage associated with the use the internal wire segment 241 is that the formation of the internal helix upon expansion of the expandable member 212 assists in capturing the embolic obstruction.

Figure 17:
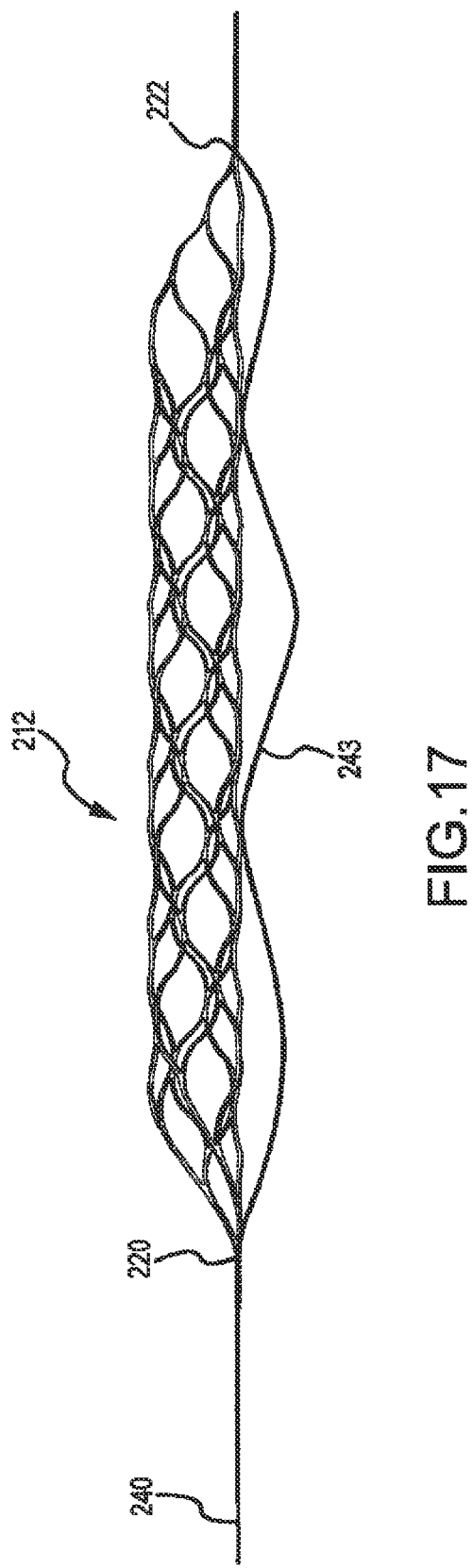
FIG. 17 illustrates an isometric view of an expandable member in another embodiment having an external wire segment.

In an alternative embodiment, as shown in FIG. 17, the pushability of the expandable member 212 during its advancement to the treatment site of a patient is enhanced by the inclusion of an external wire segment 243 that extend between the proximal end 220 and distal end 222 of the expandable member 212. In this manner, the pushing force applied by the elongate wire 240 is transmitted to both the proximal and distal ends of the expandable device. The external wire segment may be discrete element that is attached to the proximal and distal ends of the expandable member, or may preferably be a co-extension of the elongate flexible wire 240. During delivery of the expandable member 212 to the treatment site in its compressed state, the external wire segment 243 assumes a substantially straight or linear configuration so as to adequately distribute at least a part of the pushing force to the distal end 222 of the expandable member. When the expandable member 212 expands, it tends to foreshorten causing slack in the external wire segment 243 as shown in FIG. 17. An additional advantage associated with the use of the external wire segment 243 is that it directly acts on the obstruction while the expandable member 212 is expanded to assist in engaging and capturing the embolic obstruction.

Figure 18:
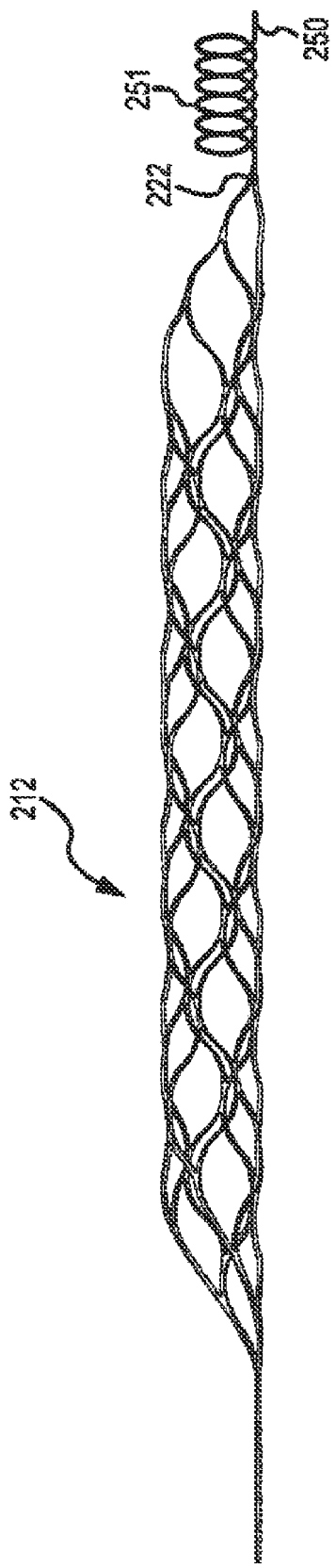
FIG. 18 illustrates an isometric view of an expandable member in yet another embodiment having a distal emboli capture device.

In yet another embodiment, a distal emboli capture device 251 is disposed on the distal wire segment 250, or otherwise attached to the distal end 222, of expandable member 212 as shown in FIG. 18. The function of the distal emboli capture device 251 is to capture emboli that may be dislodged from the embolic obstruction during the expansion of the expandable member 212 or during its removal from the patient to prevent distal embolization. In FIG. 18, the distal emboli capture device is shown as a coil. In alternative embodiments, baskets, embolic filters or other known emboli capture devices may be attached to the distal end 222 or distal wire segment 250 of expandable member 12.

Again, as with the embodiments of FIGS. 14 and 15, it is important to note that the features described in conjunction with FIGS. 16, 17 and 18 are not limited to the embodiment of FIG. 6, but are applicable to all the various embodiments disclosed herein.

Figure 19:
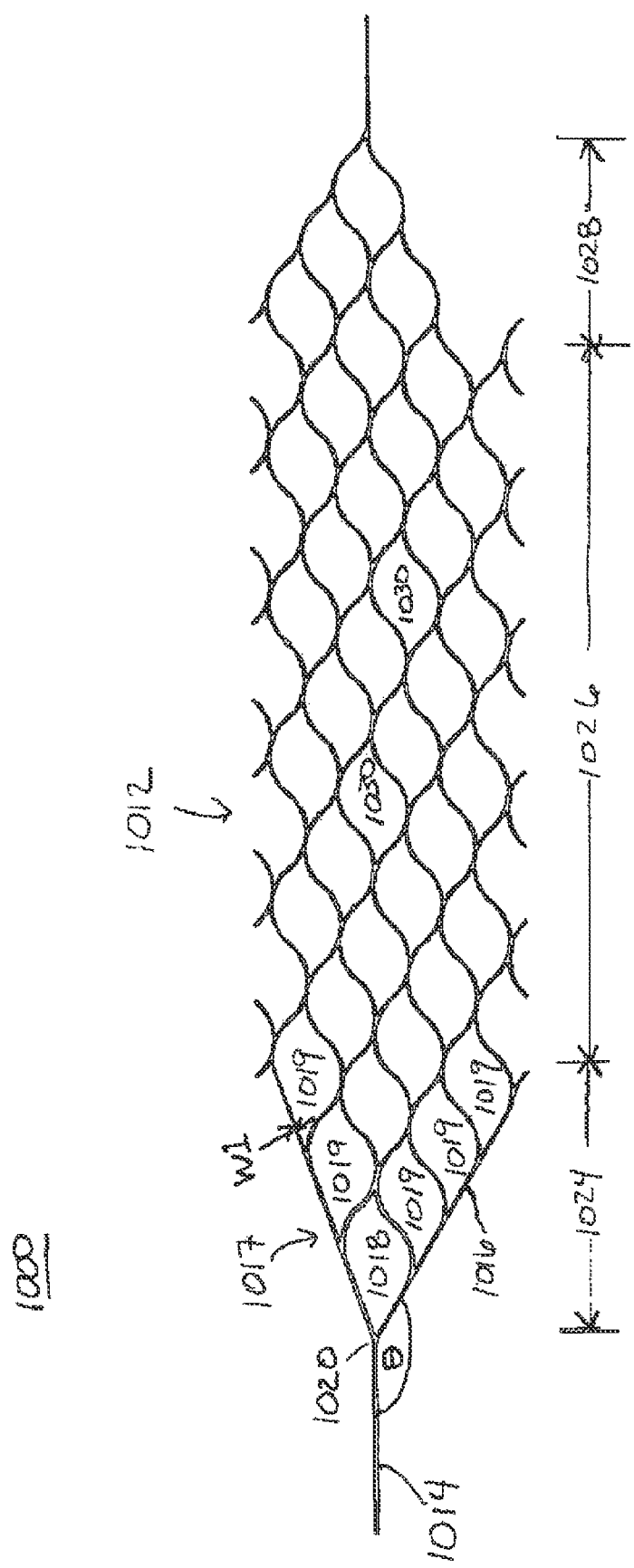
FIG. 19 illustrates a two-dimensional plane view of an expandable member of a treatment device in another embodiment.

FIG. 19 illustrates a bodily duct or vascular treatment device 1000 in accordance with another embodiment of the present invention. FIG. 19 depicts device 1000 in a two-dimensional plane view as if the device were cut and laid flat on a surface. Device 1000 includes an expandable member 1012 having a proximal end portion 1024, a cylindrical main body portion 1026 and a distal end portion 1028 with an elongate flexible wire 1014 attached to or otherwise coupled to the proximal end 1020 of the expandable member. The construction of device 1000 is similar to device 200 described above in conjunction with FIG. 6A except that the cell structures 1018 and 1019 in the proximal end portion 1024 are more closely symmetrically arranged than the cell structures in the proximal end portion 214 of device 200. The more substantial symmetrical arrangement of the cell structures in the proximal end portion 1024 of device 1000 facilitates the loading or retrieval of the expandable member 1012 into a lumen of a delivery catheter or sheath (not shown) by causing the proximal end portion 1024 to collapse more evenly during compression. The proximal wall segments 1016 of cell structures 1018 and 1019 comprise linear or substantially linear strut elements as viewed in the two dimension plane view of FIG. 19. In one embodiment, the linear strut elements 1016 are aligned to form continuous and substantially linear rail segments 1017 that extend from the proximal end 1020 of proximal end portion 1024 to a proximal-most end of main body portion 1026 (again, as viewed in the two dimension plane view of FIG. 19) and preferably are of the same length. In alternative embodiments, the angle θ between the wire segment 1014 and rail segments 1017 ranges between about 140 degrees to about 150 degrees. In one embodiment, one or both of the linear rail segments 1017 have a width dimension W1 which is greater than the width dimension of the adjacent strut segments of cell structures 1018 and/or 1019 and/or 1030. An enhanced width dimension W1 of one or both the linear rail segments 1017 further enhances the rail segments' ability to distribute forces and resist buckling when a push force is applied to them. In another implementation, one or both of the linear rail segments 1017 are provided with an enhanced thickness dimension, rather than an enhanced width dimension to achieve the same or similar result. In yet an alternative implementation, both the width and thickness dimensions of one or both of the linear rail segments 1017 are enhanced to achieve the same or similar results. In yet another implementation, the width and/or thickness dimensions of each of the rail segments 1017 differ in a manner that causes a more even compression of the proximal end portion 1024 of the expandable member 1012 when it is collapsed as it is loaded or retrieved into a delivery catheter or sheath.

Figure 20:
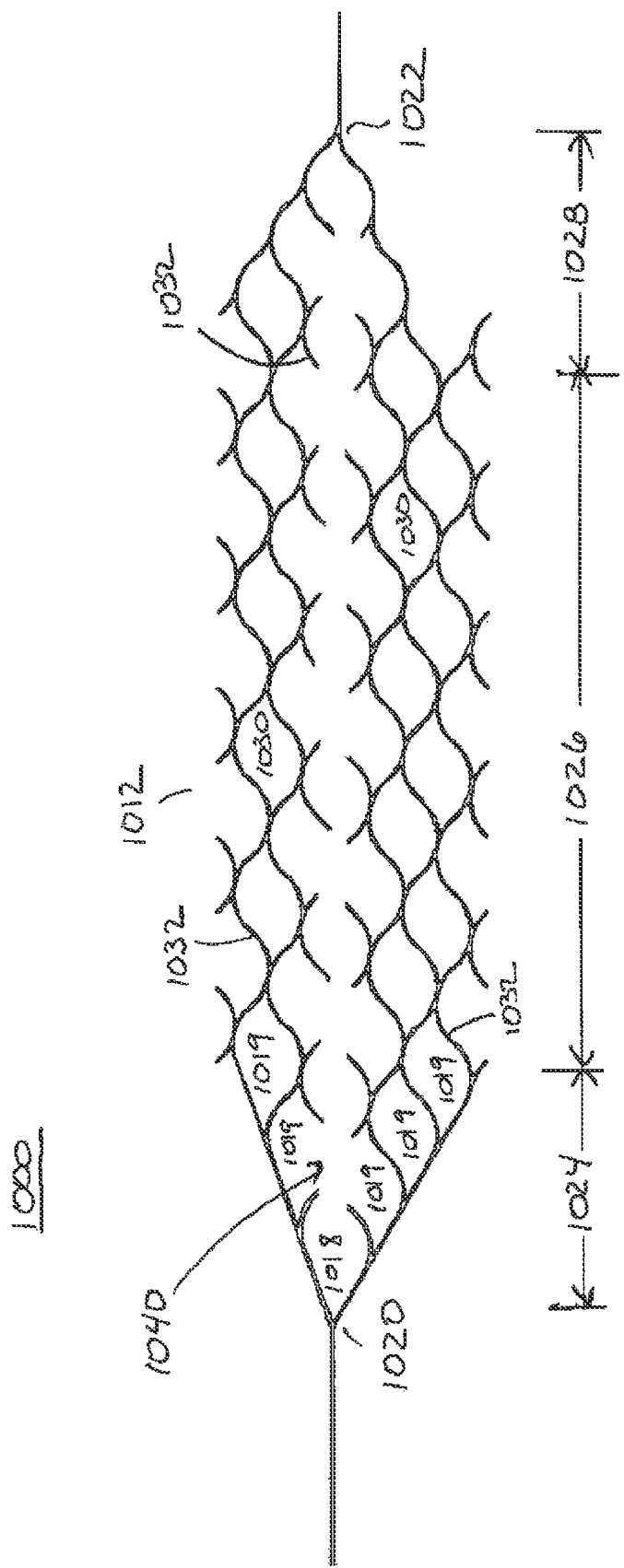
FIG. 20 illustrates the expandable member of FIG. 19 having a longitudinal slit.
Figure 21:
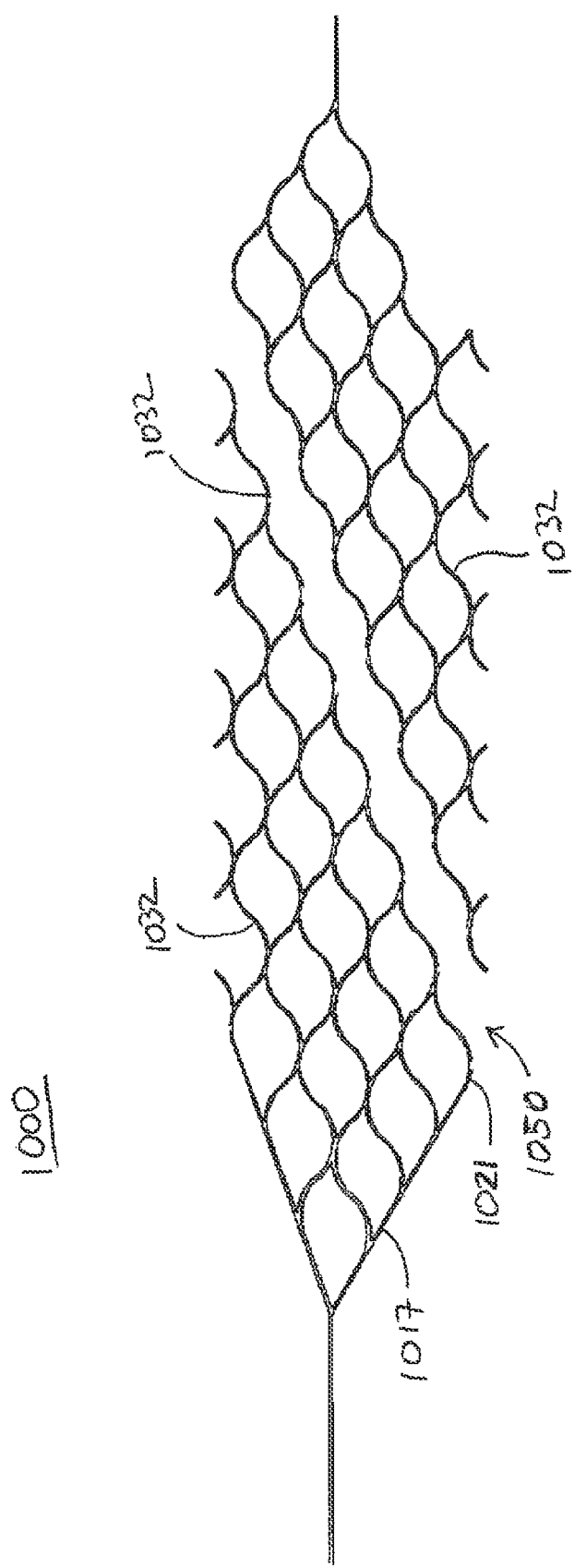
FIG. 21 illustrates the expandable member of FIG. 19 having a spiral slit.
Figure 22:
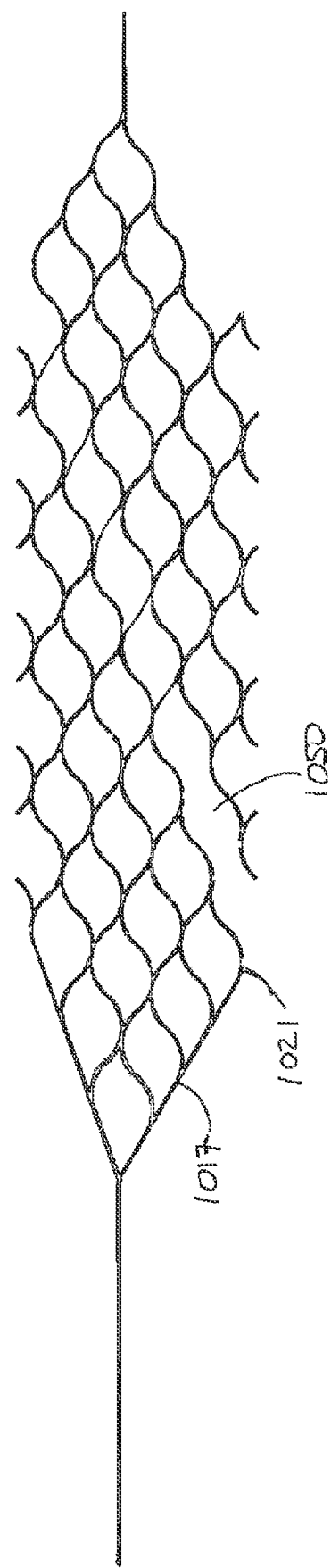
FIG. 22 illustrates the expandable member of FIG. 19 having a partial spiral slit.

Although the description that follows is directed to the embodiment of FIG. 19, it is important to note that the provision of a slit as contemplated by the embodiments of FIGS. 20-22 are applicable to all the vascular treatment devices described herein, and their numerous embodiments and modifications thereof.

Turning now to FIG. 20, the treatment device 1000 of FIG. 19 is depicted having a longitudinal slit 1040 that extends from the proximal end 1020 to the distal end 1022 of the expandable member 1012. The slit 1040 permits the cell structures 1018, 1019 and 1030 to move relative to one another in a manner that inhibits the individual strut elements 1032 of the expandable member 1012 from buckling during compression of the expandable member 1012 as it is loaded or retrieved into a delivery catheter or sheath. In alternative embodiments, slit 1040 extends less than the entire length of expandable member 1012 and is arranged to inhibit buckling of strategically important strut elements that most affect the expandable member's ability to be effectively loaded or withdrawn into a delivery catheter or sheath. For example, in one embodiment, slit 1040 is provided only in the proximal end portion 1024 of the expandable member 1012 where the likelihood of buckling or bending of struts 1032 is most likely to occur. In another embodiment, slit 1040 is provided in both the proximal end portion 1024 and the cylindrical main body portion 1026 of expandable member 1012.

FIG. 21 illustrates the treatment device 1000 of FIG. 19 having a diagonally disposed/spiral slit 1050 that extends the entire circumference of the expandable member 1012. In one embodiment, as illustrated in FIG. 21, the spiral slit 1050 originates at the distal position, or at a point adjacent to the distal position, of the proximal end portion 1024 of expandable member 1012. With respect to the embodiments having linear rail segments, such as the linear rail segments 1017 of FIG. 19, the spiral slit 1050 originates at the distal position 1021 of one of the linear rail segments 1017, or at a point distally adjacent to the distal position 1021, as shown in FIG. 21. Testing of the various vascular treatment devices described herein has shown that the occurrence of buckling tends to occur at the strut elements located adjacent to the distal positions of the proximal end portions of the expandable members. This phenomenon is exacerbated in the expandable members having proximal end portions with linear rail segments. For this reason, and with reference to FIG. 21, the originating point of spiral slit 1050 is located at or adjacent to a distal position 1021 of one of the linear rail segments 1017. An advantage of the diagonally disposed and/or spiral slit configuration of FIG. 21 is that it originates where the buckling tends to originate and further inhibits buckling of strut elements 1032 along the length of the expandable member 1012. As shown in FIG. 22, in alternative embodiments slit 1050 extends diagonally along only a portion of the circumference of the cylindrical main body portion 1026 of the expandable member 1012. In the embodiment of FIG. 22, slit 1050 originates at the distal position 1021 of linear rail segment 1017. In alternative embodiments, where buckling of individual strut elements 1032 originate at a point other than at the distal point of the proximal end portion 1024 of the expandable member 1012, the originating point of the slit 1050 is located at the origination point of the bucking (absent the slit 1050) and extends in a longitudinal direction distally therefrom.

Figure 23:
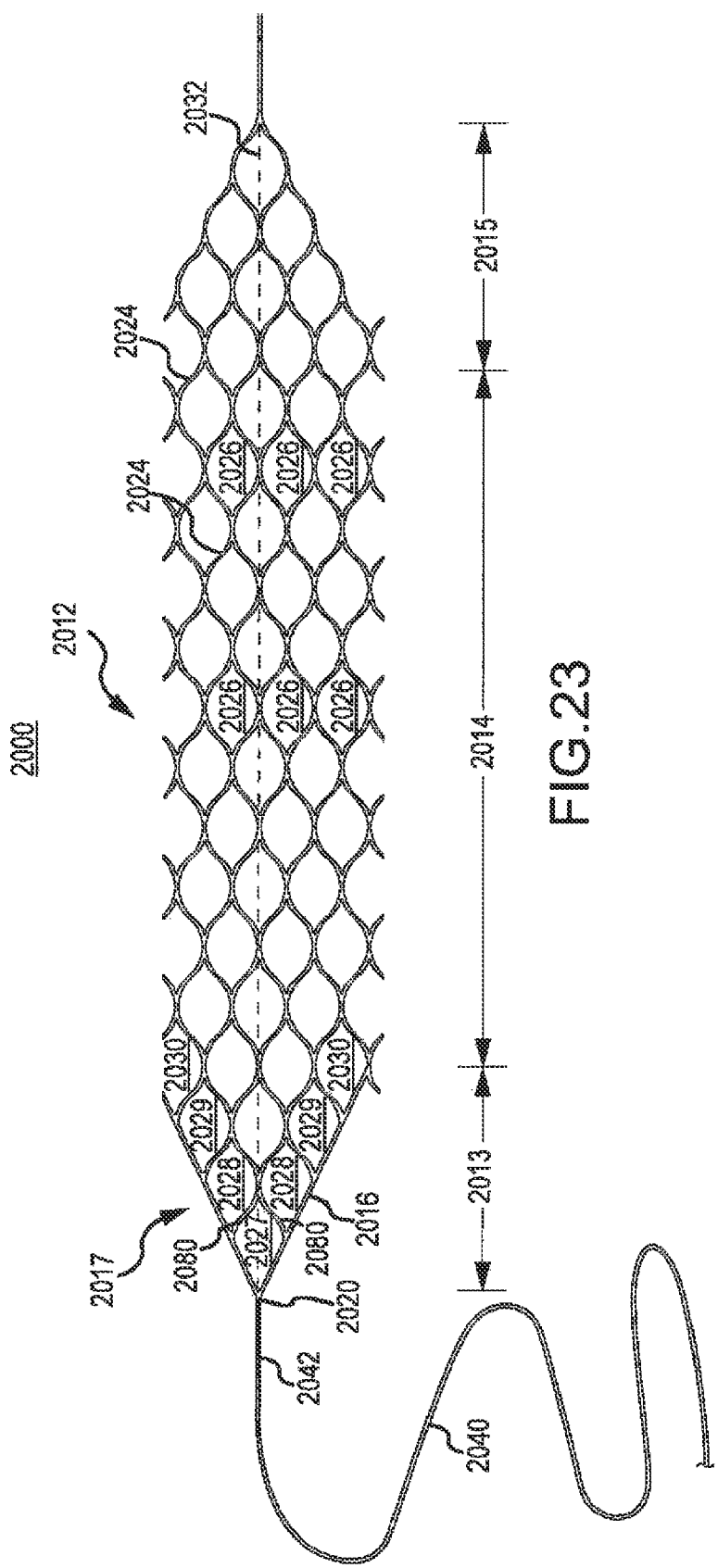
FIG. 23 illustrates a two-dimensional plane view of an expandable member of a treatment device in another embodiment.

FIG. 23 illustrates a bodily duct or vascular treatment device 2000 in accordance with an embodiment of the present invention. FIG. 23 depicts device 2000 in a two-dimensional plane view as if the device were cut and laid flat on a surface. Device 2000 includes a self-expandable member 2012 that is attached or otherwise coupled to an elongate flexible wire 2040 that extends proximally from the expandable member 2012. In one embodiment, the expandable member 2012 is made of shape memory material, such as Nitinol, and is preferably laser cut from a tube. In one embodiment, the expandable member 2012 has an integrally formed proximally extending wire segment 2042 that is used to join the elongate flexible wire 2040 to the expandable member 2012. In such an embodiment, flexible wire 2040 may be joined to wire segment 2042 by the use of solder, a weld, an adhesive, or other known attachment method. In an alternative embodiment, the distal end of flexible wire 2040 is attached directly to a proximal end 2020 of the expandable member 2012.

In the embodiment of FIG. 23, expandable member 2012 includes a plurality of generally longitudinal undulating elements 2024 with adjacent undulating elements being coupled to one another in a manner to form a plurality of circumferentially-aligned cell structures 2026. The expandable member 2012 includes a proximal end portion 2013, a cylindrical main body portion 2014 and a distal end portion 2015 with the cell structures 2026 in the main body portion 2014 extending continuously and circumferentially around a longitudinal axis 2032 of the expandable member 2012. The cell structures in the proximal end portion 2013 and distal end portion 2015 extend less than circumferentially around the longitudinal axis 2032 of the expandable member 2012. The proximal wall segments 2016 of cell structures 2027, 2028, 2029 and 2030 comprise linear or substantially linear strut elements as viewed in the two dimension plane view of FIG. 23. In one embodiment, the linear strut elements 2016 are aligned to form continuous and substantially linear rail segments 2017 that extend from the proximal end 2020 of proximal end portion 2013 to a proximal-most end of main body portion 2014 (again, as viewed in the two dimension plane view of FIG. 23) and preferably are of the same length. As described above in conjunction with FIGS. 6A and 6B, rail segments 2017 are not in fact linear but are of a curved and non-undulating shape. This configuration advantageously provides rail segments 2017 devoid of undulations thereby enhancing the rail segments' ability to distribute forces and resist buckling when a push force is applied to them. In alternative preferred embodiments, the angle θ between the wire segment 2042 or 2040, which ever the case may be, and rail segments 2017 ranges between about 140 degrees to about 150 degrees. In one embodiment the linear rail segments 2017 have a width dimension which is greater than the width dimension of the adjacent strut segments of cell structures 2027 and/or 2028 and/or 2029 and/or 2030 and/or 2026. An enhanced width of the linear rail segments 2017 further enhances the rail segments' ability to distribute forces and resist buckling when a push force is applied to the expandable member. In another implementation the linear rail segments 2017 are provided with an enhanced thickness dimension, rather than an enhanced width dimension to achieve the same or similar result. In yet an alternative implementation, both the width and thickness dimensions of the linear rail segments 2017 are enhanced to achieve the same or similar results.

In one embodiment, the width and/or thickness of the internal strut elements 2080 of proximal-most cell structure 2027 is also enhanced so as to resist buckling of these elements while the expandable member is being pushed through a sheath or delivery catheter. In one exemplary embodiment, the "as-cut" nominal widths of the enhanced strut elements 2016 and 2080 are about 0.0045 inches, while the "as-cut" nominal width of the other strut elements are about 0.003 inches.

Figure 24B:
FIG. 24B is an isometric view of the expandable member illustrated in FIG. 24A.

FIGS. 24A and 24B illustrate a vascular treatment device 3000 of another embodiment of the present invention. FIG. 24A depicts device 3000 in a two-dimensional plane view as if the device were cut and laid flat on a surface. FIG. 24B depicts the device in its manufactured and/or expanded tubular configuration. The overall design of device 3000 is similar to the design of device 2000 depicted and described above in reference to FIG. 23. The primary difference between the two designs lays in the length "L" to width "W" ratio of the cell structures 2026, 2027, 2028, 2029 and 2030. The length to width ratios of the cells structures of FIG. 24A are generally greater than the length to width ratios of the respective cell structures of FIG. 23. As illustrated, the lengths "L" of the cell structures of the device of FIG. 24A, in the "as-cut" configuration are generally greater than the lengths of the respective cell structures of FIG. 23, while the widths "W" of the cell structures of the device of FIG. 24A are generally smaller than the width of the respective cell structures of FIG. 23. As a result, the slope of the individual strut elements 2040 in the cell structures of FIG. 24A are generally smaller than the slopes of the respective strut elements in the cell structures of FIG. 23. By reducing the slope of the strut elements 2040 and leaving the other dimensional and material characteristics constant, the effective radial force along the length of the struts 2040 is reduced. The effect of such a reduction is that the summation of axial force components along lines A-A of the device of FIG. 24 more closely matches the summation of the radial force components along lines B-B as compared to the device of FIG. 23. Through experimentation, the inventors have discovered that an "as-cut" cell structure length to width ratio of greater than about 2.0, and an "expanded" cell structure length to width ratio of a greater than about 1.25, advantageously resulted in a longitudinal radial force distribution along the length of the expandable member 2012 that enhanced the expandable member's ability to be pushed through and withdrawn into a lumen of a delivery catheter.

Figure 26:
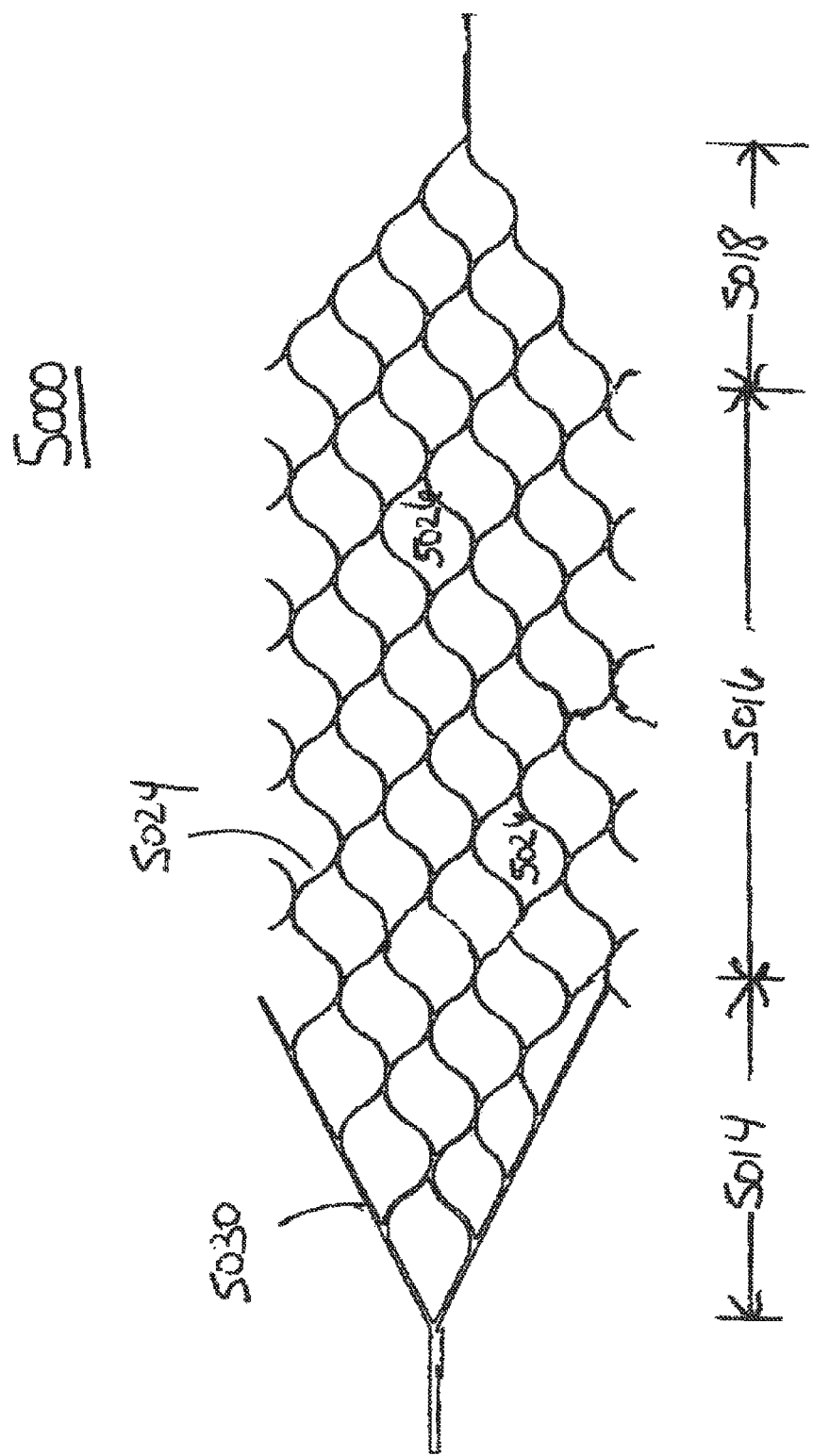
FIG. 26 illustrates a two-dimensional plane view of an expandable member of a treatment device in yet another embodiment.
Figure 27A:
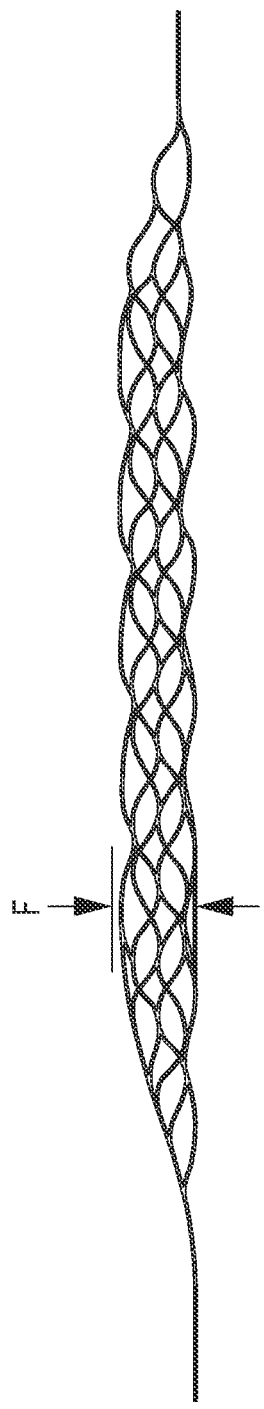
FIGS. 27A and 27B illustrate isometric side and top views, respectively, of the expandable member depicted in FIG. 26.
Figure 27B:
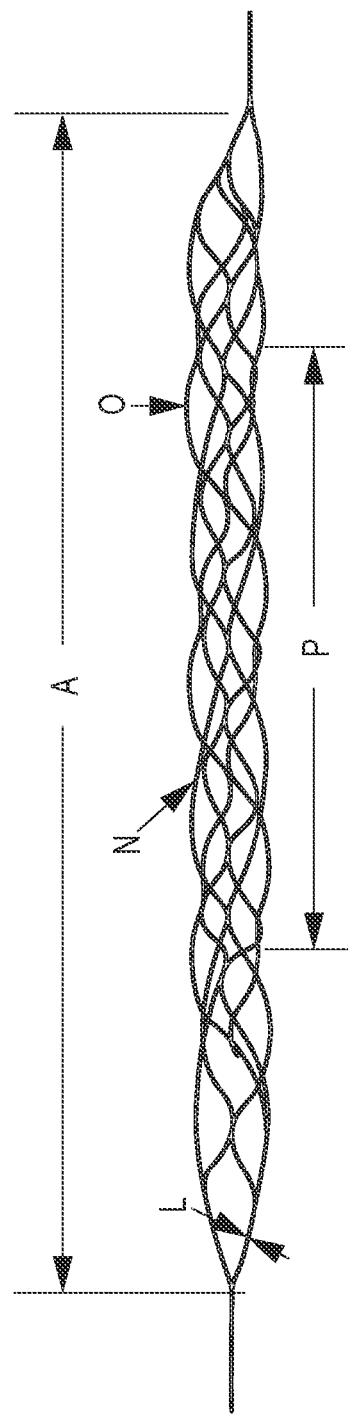

FIGS. 26, 27A and 27B illustrate an expandable member 5000 in another implementation. Expandable member 5000 includes a plurality of generally longitudinal undulating elements 5024 with adjacent undulating elements being out-of-phase with one another and connected in a manner to form a plurality of diagonally disposed cell structures 5026 angularly disposed between about 40.0 to about 50.0 degrees with respect to one another. In one implementation, the cell structures are diagonally displaced along about a 45.0 degree line. The expandable member 5000 includes a proximal end portion 5014, a cylindrical main body portion 5016 and a distal end portion 5018 with the cell structures 5026 in the main body portion 5016 extending continuously and circumferentially around a longitudinal axis of the expandable member 5000. The cell structures 5026 in the proximal end portion 5014 and distal end portion 5018 extend less than circumferentially around the longitudinal axis of the expandable member 5000. In one implementation, the expandable member has an unexpanded or crimped nominal diameter of about 1.0 millimeters and a designed maximum implantable diameter of about 4.0 millimeters.

In one embodiment, expandable member 5000 has an overall length dimension A of about 36.0±2.0 millimeters with the main body portion 5016 having a length P of about 19.0±2.0 millimeters. In one implementation the strut width dimension N and thickness dimension 0 within the main body portion 5016 are about 0.0021±0.0004 inches and about 0.0032±0.0005 inches, respectively, while the strut width dimension L of the proximal rails 5030 is about 0.0039±0.004 inches.

In use, expandable member 5000 is advanced through the tortuous vascular anatomy or bodily duct of a patient to a treatment site in an unexpanded or compressed state (not shown) of a first nominal diameter and is movable from the unexpanded state to a radially expanded state of a second nominal diameter greater than the first nominal diameter for deployment at the treatment site. In alternative exemplary embodiments the first nominal diameter (e.g., average diameter of main body portion 5016) ranges between about 0.017 to about 0.030 inches, whereas the second nominal diameter (e.g., average diameter of main body portion 5016) is between about 2.5 to about 5.0 millimeters. In one implementation, the dimensional and material characteristics of the cell structures 5026 residing in the main body portion 5016 of the expandable material 5000 are selected to produce sufficient radial force and contact interaction to cause the cell structures 5026 to engage with an embolic obstruction residing in the vascular in a manner that permits partial or full removal of the embolic obstruction from the patient. In other embodiments the dimensional and material characteristics of the cell structures 5026 in the main body portion 5016 are selected to produce a radial force per unit length of between about 0.005 N/mm to about 0.050 N/mm, preferable between about 0.010 N/mm to about 0.050 N/mm, and more preferably between about 0.030 N/mm and about 0.050 N/mm. In one embodiment, the diameter of the main body portion 5016 in a designed fully expanded implanted state is about 4.0 millimeters with the cell pattern, strut dimensions and material being selected to produce a radial force of between about 0.030 N/mm to about 0.050 N/mm when the diameter of the main body portion is reduced to 1.5 millimeters. In the same or alternative embodiment, the cell pattern, strut dimensions and material(s) are selected to produce a radial force of between about 0.010 N/mm to about 0.020 N/mm when the diameter of the main body portion is reduced to 3.0 millimeters.

Figure 29:
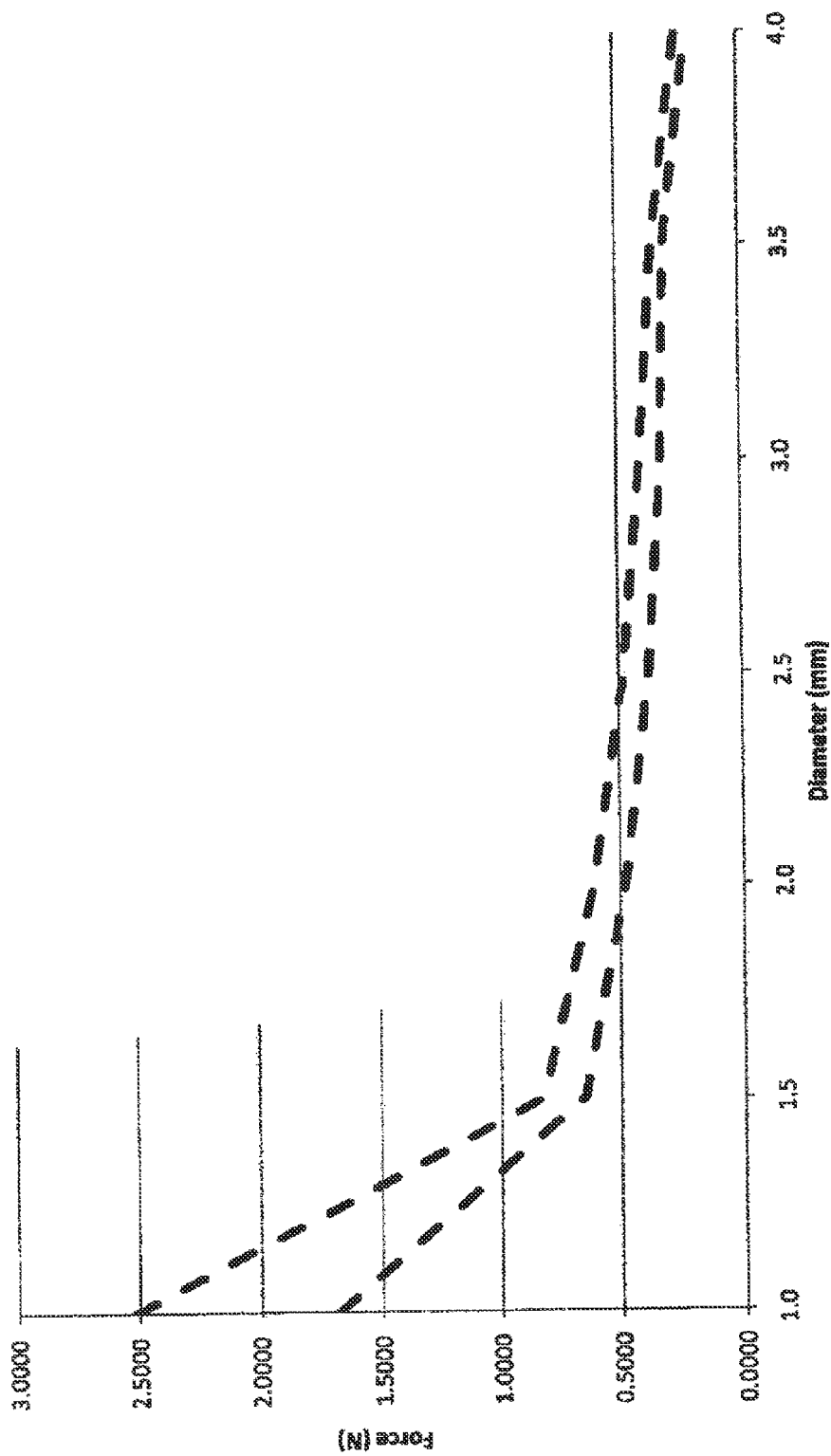
FIG. 29 is a graph representing a radial force curve of an expandable member according to one implementation.

In one implementation, as shown in the graph of FIG. 29, the cell structures are constructed to have dimensional and material characteristics to create an overall radial force exerted along the length of the expandable member 5000 of between about 1.7N and about 2.50N when the expandable member 5000 is in the compressed or crimped state. About a −1.0N to a about a −1.7N overall reduction in radial force along the length of the expandable member per millimeter of expansion occurs during about an initial 0.50 mm diametric range of expansion from the compressed or crimped state. Subsequent to the about 0.5 mm diametric range of expansion, about a −0.10N to about a −0.35N overall reduction in radial force along the length of the expandable member per millimeter of expansion occurs until a non-zero radial force value is achieved if and when the designed maximum implantable diameter is achieved. Advantageously, the expandable member 5000 exerts a relatively high radial force during its initial expansion to enhance the likelihood that the struts of expandable member engage an obstruction within the duct of a patient upon initial deployment of the device. In addition, the rate at which the radial force diminishes is initially much greater during the initial expansion of the device than during subsequent expansion. In the exemplary embodiment depicted by FIG. 29, the initial rate of reduction in the radial force during about the first 0.5 mm of expansion is about 8 to 15 times greater than the rate of reduction during subsequent expansions. An advantage of this radial force characteristic is that high radial force values can be achieved during initial deployment of the expandable member to enhance integration of the struts of the expandable member into the duct obstruction with a subsequent large reduction in radial force after the initial expansion, the large reduction facilitating or enhancing the ability of the obstruction to be removed from the duct of the patient without complications and with limited adverse interactions with the duct (e.g., less damage to the duct wall, etc.). Another advantage of the radial force characteristics depicted in FIG. 29 is that during subsequent expansions, the rate of decrease in the over radial force along the length of the expandable member decreases in a linear-like fashion at a much reduced rate providing a level of predictability of the radial force being exerted at the different expandable member diameters. Also, advantageously, the radial force exerted by the expandable member is designed to achieve a non-zero value when the expandable member is at a designed maximum implantable diameter.

While the above description contains many specifics, those specifics should not be construed as limitations on the scope of the disclosure, but merely as exemplifications of preferred embodiments thereof. For example, dimensions other than those listed above are contemplated. For example, retrieval devices having expanded diameters of any where between 1.0 and 100.0 millimeters and lengths of up to 5.0 to 10.0 centimeters are contemplated. Moreover, it is appreciated that many of the features disclosed herein are interchangeable among the various embodiments. Those skilled in the art will envision many other possible variations that are within the scope and spirit of the disclosure. Further, it is to be appreciated that the delivery of a vascular treatment device of the embodiments disclosed herein is achievable with the use of a catheter, a sheath or any other device that is capable of carrying the device with the expandable member in a compressed state to the treatment site and which permits the subsequent deployment of the expandable member at a vascular treatment site. The vascular treatment site may be (1) at the neck of an aneurysm for diverting flow and/or facilitating the placement of coils or other like structures within the sack of an aneurysm, (2) at the site of an embolic obstruction with a purpose of removing the embolic obstruction, (3) at the site of a stenosis with a purpose of dilating the stenosis to increase blood flow through the vascular, etc.

What is claimed is:

1. A clot retrieval device comprising:
an elongate self-expandable member having a length and expandable from a first delivery position to a second position, in the first delivery position the self-expandable member being in an unexpanded position and having a first nominal diameter and in the second position the self-expandable member being in a radially expanded position and having a second nominal diameter greater than the first nominal diameter, the self-expandable member adapted for deployment within a clot located in a vessel or duct of a patient as the self-expandable member transitions between the first delivery position to the second position, the self-expandable member comprising a first plurality of closed cell structures and a second plurality of closed cell structures, the self-expandable member having a proximal end portion with a proximal end and an elongate cylindrical main body portion, the proximal end portion being formed by the first plurality of closed cell structures and the elongate cylindrical main body portion being formed by the second plurality of closed cell structures, the second plurality of closed cell structures in the elongate cylindrical main body portion extending circumferentially around a longitudinal axis of the self-expandable member, the first plurality of closed cell structures in the proximal end portion extending less than circumferentially around the longitudinal axis of the self-expandable member, the first and second plurality of closed cell structures having dimensional and material characteristics that result in an overall radial force exerted along the length of the self-expandable member of between 1.70N and 2.50N when the self-expandable member has a nominal diameter of one millimeter and that further results in a −1.0N to a −1.7N overall reduction in radial force along the length of the self-expandable member per millimeter of expansion during an initial 0.50 mm diametric range of expansion from the first nominal diameter and that results in a −0.10N to a −0.35N overall reduction in radial force along the length of the expandable member per millimeter of expansion during subsequent diametric ranges of expansion.

2. A clot retrieval device according to claim 1, wherein the elongate self-expandable member has a designated maximum second nominal diameter, the radial force exerted by the elongate self-expandable member being greater than zero when expanded to the maximum second nominal diameter.

3. A clot retrieval device according to claim 1, wherein an outer-most of the first plurality of closed cell structures comprise first struts and the second plurality of closed cell structures comprise second struts, the first struts having a greater cross-sectional area than the second struts, the second struts having a thickness to width ratio of greater than one.

4. A clot retrieval device according to claim 3, wherein the second struts have a thickness to width ratio of less than 2.0.

5. A clot retrieval device according to claim 3, wherein the second struts have a thickness to width ratio of between about 1.25 and about 1.75.

6. A clot retrieval device according to claim 1, wherein an outer-most of the first plurality of closed cell structures have proximal-most wall segments that, when the self-expandable member is cut and laid flat on a surface, form first and second substantially straight rail segments that each extend from a position at or near the proximal end of the self-expandable member to a distal position at or near the elongate cylindrical main body portion.

7. A clot retrieval device according to claim 1, further comprising a third plurality of cell structures that form a distal end portion located distal to the elongate cylindrical main body portion, the third plurality of cell structures extending less than circumferentially around the longitudinal axis of the expandable member.

8. A clot retrieval device according to claim 1, wherein the first and second plurality of closed cell structures are constructed from a plurality of generally longitudinal undulating elements with adjacent undulating elements being interconnected in a manner to form diagonally disposed cell structures.

9. A clot retrieval device comprising:
an elongate self-expandable member having a length and expandable from a first delivery position to a second placement position, in the first delivery position the self-expandable member being in an unexpanded position and having a first nominal diameter and in the second position the self-expandable member being in a radially expanded position and having a second nominal diameter greater than the first nominal diameter for deployment within a clot within a vessel or duct of a patient, the self-expandable member comprising a plurality of generally longitudinal undulating elements with adjacent undulating elements being interconnected in a manner to form a first plurality of diagonally disposed closed cell structures, a second plurality of diagonally disposed closed cell structures and a third plurality of diagonally disposed closed cell structures, the self-expandable member having a proximal end portion formed by the first plurality of diagonally disposed closed cell structures, an elongate cylindrical main body portion formed by the second plurality of diagonally disposed closed cell structures and a distal end portion formed by the third plurality of diagonally disposed closed cell structures, the second plurality of diagonally disposed closed cell structures extending circumferentially around a longitudinal axis of the self-expandable member, each of the first and third plurality of diagonally disposed cell structures extending less than circumferentially around the longitudinal axis of the self-expandable member, the first, second and third plurality of diagonally disposed closed cell structures having dimensional and material characteristics that result in an overall radial force exerted along the length of the self-expandable member of between 1.70N and 2.50N when the self-expandable member has a nominal diameter of one millimeter and that further results in a −1.0N to a −1.7N overall reduction in radial force along the length of the expandable member per millimeter of expansion during an initial 0.50 mm diametric range of expansion from the first nominal diameter and that results in a −0.10N to a −0.35N overall reduction in radial force along the length of the self-expandable member per millimeter of expansion during subsequent diametric ranges of expansion.

10. A clot retrieval device according to claim 9, wherein the elongate self-expandable member has a designated maximum second nominal diameter, the radial force exerted by the elongate self-expandable member being greater than zero when expanded to the maximum second nominal diameter.

11. A clot retrieval device according to claim 9, wherein an outer-most of the first plurality of closed cell structures have proximal-most wall segments that, when the self-expandable member is cut and laid flat on a surface, form first and second substantially straight rail segments that each extend from a position at or near the proximal end of the self-expandable member to a position at or near the elongate cylindrical main body portion.

* * * * *